US010081674B2

(12) United States Patent
Barbour et al.

(10) Patent No.: US 10,081,674 B2
(45) Date of Patent: Sep. 25, 2018

(54) ANTIBODIES RECOGNIZING α-SYNUCLEIN

(71) Applicant: PROTHENA BIOSCIENCES LIMITED, Dublin (IE)

(72) Inventors: Robin Barbour, Walnut Creek, CA (US); Kate Dora Games Thiel, Belmont, CA (US); Tarlochan S. Nijjar, Orinda, CA (US)

(73) Assignee: PROTHENA BIOSCIENCES LIMITED, Dublin (IE)

( * ) Notice: Subject to any disclaimer, the term of this patent is extended or adjusted under 35 U.S.C. 154(b) by 0 days.

(21) Appl. No.: 15/429,962

(22) Filed: Feb. 10, 2017

(65) Prior Publication Data

US 2017/0152310 A1 Jun. 1, 2017

Related U.S. Application Data

(62) Division of application No. 14/049,169, filed on Oct. 8, 2013, now Pat. No. 9,605,056.

(60) Provisional application No. 61/711,204, filed on Oct. 8, 2012, provisional application No. 61/719,281, filed on Oct. 26, 2012, provisional application No. 61/840,432, filed on Jun. 27, 2013, provisional application No. 61/872,366, filed on Aug. 30, 2013.

(51) Int. Cl.
*C07K 16/00* (2006.01)
*C07K 16/18* (2006.01)

(52) U.S. Cl.
CPC .......... *C07K 16/18* (2013.01); *C07K 2317/14* (2013.01); *C07K 2317/24* (2013.01); *C07K 2317/34* (2013.01); *C07K 2317/56* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS 6,719,971 B1 4/2004 Carter et al.
6,881,557 B2 4/2005 Foote et al.
(Continued)

FOREIGN PATENT DOCUMENTS

EP 2234600 B1 8/2014
WO WO 2004/039234 A2 5/2004
(Continued)

OTHER PUBLICATIONS

Roche Data Sheet, "Herceptin 140625" Prepared Jun. 25, 2014.
(Continued)

*Primary Examiner* — Adam M Weidner
*Assistant Examiner* — Aurora M Fontainhas
(74) *Attorney, Agent, or Firm* — Alston & Bird LLP

(57) ABSTRACT

The invention provides monoclonal antibody 5C1 and related antibodies. The 5C1 antibody binds to an epitope within residues 118-126 of α-synuclein. The antibodies of the invention are useful, for example, for treating and/or diagnosing disorders associated with α-synuclein, particularly accumulation of α-synuclein deposits. Such disorders include Lewy body diseases, such as Parkinson's disease, Diffuse Lewy Body Disease (DLBD), Lewy body variant of Alzheimer's disease (LBV), Combined Alzheimer's and Parkinson disease, pure autonomic failure and multiple system atrophy (MSA).

26 Claims, 17 Drawing Sheets
(8 of 17 Drawing Sheet(s) Filed in Color)
Specification includes a Sequence Listing.

5C1-VH

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m5C1VH | Q | V | Q | L | Q | Q | S | G | A | E | L | A | K | P | G | T | S | V | Q | M |

| Kabat Numbering | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| m5C1VH | S | C | K | A | S | G | Y | T | F | T | *N* | *Y* | *W* | *M* | *N* | *W* | I | K | A | R |

| Kabat Numbering | 41 | 42 | 43 | 44 | 45 | 46 | 47 | 48 | 49 | 50 | 51 | 52 | 52A | 53 | 54 | 55 | 56 | 57 | 58 | 59 |
|---|---|---|---|---|---|---|---|---|---|---|---|---|---|---|---|---|---|---|---|---|
| m5C1VH | P | G | Q | G | L | E | W | I | G | *A* | *T* | *N* | *P* | *N* | *N* | *G* | *Y* | *T* | *D* | *Y* |

| Kabat Numbering | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|
| m5C1VH | *N* | *Q* | *R* | *F* | *K* | *D* | K | A | I | L | T | A | D | K | S | S | N | T | A | Y |

| Kabat Numbering | 80 | 81 | 82 | 82A | 82B | 82C | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|
| m5C1VH | M | H | L | S | S | L | T | S | E | D | S | A | V | Y | F | C | A | S | *G* | *G* |

| Kabat Numbering | 97 | 98 | 99 | 100 | 101 | 102 | 103 | 104 | 105 | 106 | 107 | 108 | 109 | 110 | 111 | 112 | 113 | 114 |
|---|---|---|---|---|---|---|---|---|---|---|---|---|---|---|---|---|---|---|
| m5C1VH | *H* | *L* | *A* | - | - | *Y* | W | G | Q | G | T | V | V | T | V | S | A | - |

(56) References Cited

U.S. PATENT DOCUMENTS

| | | | |
|---|---|---|---|
| 7,022,500 | B1 | 4/2006 | Queen et al. |
| 7,358,331 | B2 | 4/2008 | Chilcote et al. |
| 7,566,771 | B1 | 7/2009 | Adair et al. |
| 7,657,380 | B2 | 2/2010 | Lazar et al. |
| 7,674,599 | B2 | 3/2010 | Chilcote et al. |
| 7,910,333 | B2 | 3/2011 | Chilcote et al. |
| 7,919,088 | B2 | 4/2011 | Schenk et al. |
| 8,092,801 | B2 | 1/2012 | Schenk et al. |
| 8,609,820 | B2 | 12/2013 | Saldanha et al. |
| 8,790,644 | B2 | 7/2014 | Saldanha et al. |
| 9,217,030 | B2 | 12/2015 | Saldanha et al. |
| 9,234,031 | B2 | 1/2016 | Saldanha et al. |
| 9,556,259 | B2 | 1/2017 | Saldanha et al. |
| 9,605,056 | B2 | 3/2017 | Barbour et al. |
| 9,670,273 | B2 | 6/2017 | Saldanha et al. |
| 2006/0008883 | A1 | 1/2006 | Lazar et al. |
| 2008/0014194 | A1 | 1/2008 | Schenk et al. |
| 2009/0010924 | A1 | 1/2009 | Wu et al. |
| 2009/0202432 | A1 | 8/2009 | Schenk et al. |
| 2009/0208487 | A1 | 8/2009 | Schenk et al. |
| 2010/0031377 | A1 | 2/2010 | Schenk et al. |
| 2010/0086545 | A1 | 4/2010 | Schenk et al. |
| 2010/0098712 | A1 | 4/2010 | Adler et al. |
| 2010/0203631 | A1 | 8/2010 | Chilcote et al. |
| 2011/0052498 | A1 | 3/2011 | Lannfelt et al. |
| 2012/0204275 | A1 | 8/2012 | Schenk |
| 2012/0276019 | A1 | 11/2012 | Charles et al. |
| 2014/0127131 | A1 | 5/2014 | Barbour et al. |
| 2014/0275495 | A1 | 9/2014 | Saldanha et al. |
| 2015/0024433 | A1 | 1/2015 | Saldanha et al. |
| 2015/0056187 | A1 | 2/2015 | Saldanha et al. |
| 2015/0079074 | A1 | 3/2015 | Garidel et al. |
| 2015/0259404 | A1 | 9/2015 | Barbour et al. |
| 2016/0251416 | A1 | 9/2016 | Saldanha et al. |
| 2018/0016329 | A1 | 1/2018 | Saldanha et al. |

FOREIGN PATENT DOCUMENTS

| | | | |
|---|---|---|---|
| WO | WO 2004/041067 | | 5/2004 |
| WO | WO 2005/047860 | A2 | 5/2005 |
| WO | WO 2007/011907 | A2 | 1/2007 |
| WO | WO 2008/011348 | A2 | 1/2008 |
| WO | WO 2008/103472 | A2 | 8/2008 |
| WO | WO 2008/116103 | A2 | 9/2008 |
| WO | WO 2010/069603 | A1 | 6/2010 |
| WO | WO 2011/090720 | A2 | 7/2011 |
| WO | WO 2011/107544 | A1 | 9/2011 |
| WO | WO 2011/127324 | A2 | 10/2011 |
| WO | WO 2011/155607 | A1 | 12/2011 |
| WO | WO 2011/156328 | A1 | 12/2011 |
| WO | WO 2012/009631 | A1 | 1/2012 |
| WO | WO 2012/160536 | A1 | 11/2012 |
| WO | WO 2012/177997 | A1 | 12/2012 |
| WO | WO 2013/063516 | A1 | 5/2013 |
| WO | WO 2013/066866 AI | | 5/2013 |
| WO | WO 2013/112945 | A1 | 8/2013 |
| WO | WO 2014/033074 | A1 | 3/2014 |
| WO | WO 2014/058924 | A2 | 4/2014 |
| WO | WO 2015/001504 | A2 | 1/2015 |
| WO | WO 2015/155694 | A1 | 10/2015 |

OTHER PUBLICATIONS

Xolair, "Highlights of Prescribing Information", Genentech, Inc. (2003).

Choi, et al., "Fine epitope mapping of monoclonal antibodies specific to human alpha-synuclein," Neurosci Lett., 17;397(1-2):53-58 (2006) Abstract only.

Daugherty, et al., "Formulation and Delivery Issues for Monoclonal Antibody Therapeutics," *Advanced Drug Delivery Reviews*, 58(5-6):686-42 (2006) with permission Elsevier.

EP 12844433.8 European Search Report dated Feb. 17, 2015.

EP 13740871.2 European Search Report dated Jun. 3, 2015.

EP13845625 European Extended Search Report dated Jul. 18, 2016.

Finlay et al., "Affinity Maturation of a Humanized Rat Antibody for Anti-RAGE Therapy: Comprehensive Mutagenesis Reveals a Hight Level of Mutational Plasticity Both Inside and Outside the Complementarity-Determining Regions", *J.Mol. Biol.*, 388, pp. 541-558, (2009).

Genbank Accession No. 3NFP A, "Chain A, Crystal Structure of the Fab Fragment of Therapeutic Antibody Daclizumab in Complex With Il-2ra (cd25) Ectodomain," Oct. 19, 2013.

Genbank Accession No. AAC28255.1, "Immunoglobulin kappa light chain [Mus musculus]," Dec. 15, 1999.

Genbank Accession No. AAF88044.1, "Immunoglobulin heavy chain variable regions [Mus musculus]," Jul. 27, 2000.

Gonzalas, et al., "SDR grafting of a murine antibody using multiple human germine templates to minimize its immunogenicity," Molecular Immunology, 41:863-872 (2004).

Hackett, et al., "Recombinant Mouse-Human Chimeric Antibodies as Calibrators in Immunoassays That Measure Antibodies to *Toxoplasma gondii,*" *J. Clin. Microbiol.*, vol. 36, No. 5, pp. 1277-1284.

Jones et al., "Deimmunization of Monoclonal Antibodies," *Therapeutic Antibodies: Methods and Protocols*, 525:405-423, (2009).

LBD Association, Inc. 2013, "Incidence of lewy body dementias in a general population", http://222.lbda.org.

Masliah et al., "Effects of α-Synuclein Immunization in a Mouse Model of Parkinson's Disease", *Neuron*, 46:857-866, (2005).

Masliah et al., "Passive Immunization Reduced Behavioral and Neuropathological Deficits in an Alpha-Synuclein Transgenic Model of Lewy Body Disease", *PLoS ONE*, 6(4):e19338, pp. 1-17, (Apr. 2011).

Mihara, et al., "CTLA4Ig inhibits T cell-dependent B-cell maturation in murine systemic lupus erythematosus, " J. Clin. Invest., vol. 106, No. 1, pp. 91-101 (2000).

Nasstrom, et al., "Antibodies against Alpha-synuclein Reduce Oligomerization in Living Cells," *PLoS ONE*, vol. 6, Issue 10, e27230 (Oct. 2011).

PCT/IB2014/062806 International Preliminary Report on Patentability dated Jan. 5, 2016.

PCT/IB2014/062806 International Search Report and Written Opinion of the International Searching Authority dated Apr. 24, 2015.

PCT/IB2014/062806 Invitation to Pay Additional Fees and Where Applicable Protest Fee dated Oct. 29, 2014.

PCT/IB2015/052524 International Preliminary Report on Patentability dated Oct. 12, 2016.

PCT/IB2015/052524 Search Report and Written Opinion dated Jul. 3, 2015.

PCT/US2002/062290 Written Opinion and Search Report dated Jan. 28, 2013.

PCT/US2012/062290 International Preliminary Report on Patentability dated Apr. 29, 2014.

PCT/US2013/023307 International Preliminary Report on Patentability and Written Opinion dated Jul. 29, 2014.

PCT/US2013/023307 Written Opinion and Search Report dated May 13, 2013.

PCT/US2013/063945 International Preliminary Report on Patentability dated Apr. 8, 2015.

PCT/US2013/063945 Invitation to Pay Additional Fees dated Feb. 6, 2014.

PCT/US2013/063945 Written Opinion and Search Report dated Apr. 22, 2014.

U.S. Appl. No. 14/049,169 Examiner Initiated Interview Summary dated Feb. 10, 2015.

U.S. Appl. No. 14/049,169 Examiner Initiated Interview Summary dated Oct. 2, 2015.

U.S. Appl. No. 14/049,169 Examiner Initiated Interview Summary dated Nov. 1, 2016.

U.S. Appl. No. 14/049,169 Final Office Action and Telephone Interview dated Oct. 2, 2015.

U.S. Appl. No. 14/049,169 Non-Final Office Action dated Mar. 30, 2016.

U.S. Appl. No. 14/049,169 Non-Final Office Action dated Feb. 10, 2015.

U.S. Appl. No. 14/049,169 Notice of Allowance dated Nov. 1, 2016.

(56) References Cited

OTHER PUBLICATIONS

U.S. Appl. No. 14/156,441 Examiner Initiated Interview Summary dated Nov. 10, 2014.
U.S. Appl. No. 14/156,441 Final Office Action dated Jun. 8, 2016.
U.S. Appl. No. 14/156,441 Notice of Allowance dated Sep. 20, 2016.
U.S. Appl. No. 14/322,797 Non-Final Office Action dated Jan. 3, 2017.
U.S. Appl. No. 14/322,797 Restriction Requirement dated Aug. 29, 2016.
U.S. Appl. No. 14/340,342 Non-Final Office Action dated Mar. 3, 2015.
U.S. Appl. No. 14/340,555 Non-Final Office Action dated Apr. 8, 2015.
U.S. Appl. No. 14/937,792 Examiner Initiated Interview Summary dated Feb. 2, 2017.
U.S. Appl. No. 14/937,792 Examiner Initiated Interview Summary dated Aug. 30, 2016.
U.S. Appl. No. 14/937,792 Non-Final Office Action dated Aug. 30, 2016.
U.S. Appl. No. 14/937,792 Notice of Allowance dated Feb. 2, 2017.
U.S. Appl. No. 12/156,441 Non-Final Office Action dated Nov. 10, 2014.
U.S. Appl. No. 14/049,169 Restriction Requirement dated Jul. 16, 2014.
Wang, "Advances in the production of human monoclonal antibodies," Antibody Technology Journal, 1: 1-4 (2011).
Wang, et at., "Antibody Structure, Instability, and Formulation", Journal of Pharmaceutical Sciences, vol. 96:1 pp. 1-26 (Jan. 2007).
Wang, W., "Instability, stabilization, and formulation of liquid protein pharmaceuticals," Int. J. Pharmaceutics, 185(2):129-188 (1999).
Warne, et al., "Development of high concentration protein biopharmaceuticals: The use of platform approaches in formulation development," *European Journal of Pharmaceutics and Biopharmaceutics*, 78:208-212 (2011).
Yang, et al., "Structural basis of immunosuppression by the therapeutic antibody daclizumab," *Cell Research*, 20:1361-1371 (2010).
Zhang et al., "Conformation-dependent scFv antibodies specifically recognize the oligomers assembled from various amyloids and show colocalization of amyloid fibrils with oligomers in patients with amyloidoses," Biochimica et Biophysica Acta (BBA)—Protein & Proteomics, 1814(2):1703-1712, (2011).
U.S. Appl. No. 15/387,580 Notice of Allowance dated Sep. 28, 2017.
U.S. Appl. No. 14/322,797 Final Office Action dated Jul. 19, 2017.
Mahler, et al., "Trends n Formulation and Drug Delivery for Antibodies", Process Scale Purification of Antibodies, Second Edition, Edited by Uwe Gottschalk, 2017 John Wiley & Sons, Inc. Published 2017 by John Wiley & Sons, Inc.
U.S. Appl. No. 14/322,797 Non-Final Office Action dated Mar. 2, 2018.

5C1-VH

| | | | | | | | | | | | | | | | | | | | | |
|---|---|---|---|---|---|---|---|---|---|---|---|---|---|---|---|---|---|---|---|---|
| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
| m5C1VH | Q | V | Q | L | Q | Q | S | G | A | E | L | A | K | P | G | T | S | V | Q | M |

| | | | | | | | | | | | | | | | | | | | | |
|---|---|---|---|---|---|---|---|---|---|---|---|---|---|---|---|---|---|---|---|---|
| Kabat Numbering | 21 | 22 | 23 | 24 | 25 | 26 | 27 | 28 | 29 | 30 | 31 | 32 | 33 | 34 | 35 | 36 | 37 | 38 | 39 | 40 |
| m5C1VH | S | C | K | A | S | G | Y | T | F | T | ***N*** | ***Y*** | ***W*** | ***M*** | ***N*** | ***W*** | I | K | A | R |

| | | | | | | | | | | | | | | | | | | | | |
|---|---|---|---|---|---|---|---|---|---|---|---|---|---|---|---|---|---|---|---|---|
| Kabat Numbering | 41 | 42 | 43 | 44 | 45 | 46 | 47 | 48 | 49 | 50 | 51 | 52 | 52A | 53 | 54 | 55 | 56 | 57 | 58 | 59 |
| m5C1VH | P | G | Q | G | L | E | W | I | G | ***A*** | ***T*** | ***N*** | ***P*** | ***N*** | ***N*** | ***G*** | ***Y*** | ***T*** | ***D*** | ***Y*** |

| | | | | | | | | | | | | | | | | | | | | |
|---|---|---|---|---|---|---|---|---|---|---|---|---|---|---|---|---|---|---|---|---|
| Kabat Numbering | 60 | 61 | 62 | 63 | 64 | 65 | 66 | 67 | 68 | 69 | 70 | 71 | 72 | 73 | 74 | 75 | 76 | 77 | 78 | 79 |
| m5C1VH | ***N*** | ***Q*** | ***R*** | ***F*** | ***K*** | ***D*** | K | A | I | L | T | A | D | K | S | S | N | T | A | Y |

| | | | | | | | | | | | | | | | | | | | | |
|---|---|---|---|---|---|---|---|---|---|---|---|---|---|---|---|---|---|---|---|---|
| Kabat Numbering | 80 | 81 | 82 | 82A | 82B | 82C | 83 | 84 | 85 | 86 | 87 | 88 | 89 | 90 | 91 | 92 | 93 | 94 | 95 | 96 |
| m5C1VH | M | H | L | S | S | L | T | S | E | D | S | A | V | Y | F | C | A | S | ***G*** | ***G*** |

| | | | | | | | | | | | | | | | | | | |
|---|---|---|---|---|---|---|---|---|---|---|---|---|---|---|---|---|---|---|
| Kabat Numbering | 97 | 98 | 99 | 100 | 101 | 102 | 103 | 104 | 105 | 106 | 107 | 108 | 109 | 110 | 111 | 112 | 113 | 114 |
| m5C1VH | ***H*** | ***L*** | ***A*** | ***~*** | ***~*** | ***Y*** | W | G | Q | G | T | V | V | T | V | S | A | ~ |

| | | | | | | | | | | | | | | | | | | | | |
|---|---|---|---|---|---|---|---|---|---|---|---|---|---|---|---|---|---|---|---|---|
| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
| m5C1VL | D | V | V | M | T | Q | I | P | L | Y | L | S | V | S | P | G | D | Q | A | S |

| | | | | | | | | | | | | | | | | | | | | |
|---|---|---|---|---|---|---|---|---|---|---|---|---|---|---|---|---|---|---|---|---|
| Kabat Numbering | 21 | 22 | 23 | 24 | 25 | 26 | 27 | 27A | 27B | 27C | 27D | 27E | 27F | 28 | 29 | 30 | 31 | 32 | 33 | 34 |
| m5C1VL | I | S | C | *R* | *S* | *S* | *Q* | *S* | *L* | *F* | *H* | *S* | ~ | *K* | *G* | *N* | *T* | *Y* | *L* | *H* |

| | | | | | | | | | | | | | | | | | | | | |
|---|---|---|---|---|---|---|---|---|---|---|---|---|---|---|---|---|---|---|---|---|
| Kabat Numbering | 35 | 36 | 37 | 38 | 39 | 40 | 41 | 42 | 43 | 44 | 45 | 46 | 47 | 48 | 49 | 50 | 51 | 52 | 53 | 54 |
| m5C1VL | W | Y | L | Q | K | P | G | Q | S | P | K | L | L | I | N | *R* | *V* | *S* | *N* | *R* |

| | | | | | | | | | | | | | | | | | | | | |
|---|---|---|---|---|---|---|---|---|---|---|---|---|---|---|---|---|---|---|---|---|
| Kabat Numbering | 55 | 56 | 57 | 58 | 59 | 60 | 61 | 62 | 63 | 64 | 65 | 66 | 67 | 68 | 69 | 70 | 71 | 72 | 73 | 74 |
| m5C1VL | *F* | *S* | G | V | P | D | R | F | S | G | S | G | S | G | T | D | F | T | L | K |

| | | | | | | | | | | | | | | | | | | | | |
|---|---|---|---|---|---|---|---|---|---|---|---|---|---|---|---|---|---|---|---|---|
| Kabat Numbering | 75 | 76 | 77 | 78 | 79 | 80 | 81 | 82 | 83 | 84 | 85 | 86 | 87 | 88 | 89 | 90 | 91 | 92 | 93 | 94 |
| m5C1VL | I | S | G | V | E | A | E | D | L | G | V | Y | F | C | *S* | *Q* | *S* | *A* | *H* | *V* |

| | | | | | | | | | | | | | |
|---|---|---|---|---|---|---|---|---|---|---|---|---|---|
| Kabat Numbering | 95 | 96 | 97 | 98 | 99 | 100 | 101 | 102 | 103 | 104 | 105 | 106 | 107 |
| m5C1VL | *P* | *W* | *T* | F | G | G | G | T | K | L | E | I | R |

| Humanized 5C1 Vh Regions | | | | | | | | | |
|---|---|---|---|---|---|---|---|---|---|
| Kabat # | Linear # | FR or CDR | Murine 5C1 (SEQ ID NO: 9) | Hu VH Acceptor FR (SEQ ID NO: 13) | 5C1 H1 (SEQ ID NO: 14) | 5C1 H2 (SEQ ID NO: 15) | 5C1 H3 (SEQ ID NO: 16) | 5C1 H4 (SEQ ID NO: 17) | 5C1 H5 (SEQ ID NO: 18) |
| | | | | Acc#AAY42876.1 | | | | | |
| 1 | 1 | Fr1 | Q | Q | Q | Q | Q | Q | Q |
| 2 | 2 | Fr1 | V | V | V | V | V | V | V |
| 3 | 3 | Fr1 | Q | Q | Q | Q | Q | Q | Q |
| 4 | 4 | Fr1 | L | L | L | L | L | L | L |
| 5 | 5 | Fr1 | Q | V | V | V | V | V | V |
| 6 | 6 | Fr1 | Q | Q | Q | Q | Q | Q | Q |
| 7 | 7 | Fr1 | S | S | S | S | S | S | S |
| 8 | 8 | Fr1 | G | G | G | G | G | G | G |
| 9 | 9 | Fr1 | A | A | A | A | A | A | A |
| 10 | 10 | Fr1 | E | E | E | E | E | E | E |
| 11 | 11 | Fr1 | L | V | L | L | L | L | L |
| 12 | 12 | Fr1 | A | K | K | K | K | K | K |
| 13 | 13 | Fr1 | K | K | K | K | K | K | K |
| 14 | 14 | Fr1 | P | P | P | P | P | P | P |
| 15 | 15 | Fr1 | G | G | G | G | G | G | G |
| 16 | 16 | Fr1 | T | S | S | S | S | S | S |
| 17 | 17 | Fr1 | S | S | S | S | S | S | S |
| 18 | 18 | Fr1 | V | V | V | V | V | V | V |
| 19 | 19 | Fr1 | Q | K | K | K | K | K | K |
| 20 | 20 | Fr1 | M | V | V | V | V | V | V |
| 21 | 21 | Fr1 | S | S | S | S | S | S | S |
| 22 | 22 | Fr1 | C | C | C | C | C | C | C |
| 23 | 23 | Fr1 | K | K | K | K | K | K | K |
| 24 | 24 | Fr1 | A | A | A | A | A | A | A |
| 25 | 25 | Fr1 | S | S | S | S | S | S | S |
| 26 | 26 | Fr1 | G | G | G | G | G | G | G |
| 27 | 27 | Fr1 | Y | G | Y | Y | Y | Y | Y |
| 28 | 28 | Fr1 | T | T | T | T | T | T | T |
| 29 | 29 | Fr1 | F | F | F | F | F | F | F |
| 30 | 30 | Fr1 | T | N | T | T | T | T | T |
| 31 | 31 | CDR-H1 | N | N | N | N | N | N | N |
| 32 | 32 | CDR-H1 | Y | Y | Y | Y | Y | Y | Y |
| 33 | 33 | CDR-H1 | W | A | W | W | W | W | W |

FIG. 10B

| Humanized 5C1 Vh Regions | | | | | | | | | |
|---|---|---|---|---|---|---|---|---|---|
| Kabat # | Linear # | FR or CDR | Murine 5C1 (SEQ ID NO: 9) | Hu VH Acceptor FR (SEQ ID NO: 13) | 5C1 H1 (SEQ ID NO: 14) | 5C1 H2 (SEQ ID NO: 15) | 5C1 H3 (SEQ ID NO: 16) | 5C1 H4 (SEQ ID NO: 17) | 5C1 H5 (SEQ ID NO: 18) |
| 34 | 34 | CDR-H1 | M | I | M | M | M | M | M |
| 35 | 35 | CDR-H1 | N | N | N | N | N | N | N |
| 35A | | CDR-H1 | _ | _ | _ | _ | _ | _ | _ |
| 35B | | CDR-H1 | _ | _ | _ | _ | _ | _ | _ |
| 36 | 36 | Fr2 | W | W | W | W | W | W | W |
| 37 | 37 | Fr2 | I | V | V | V | V | V | V |
| 38 | 38 | Fr2 | K | R | R | R | R | R | R |
| 39 | 39 | Fr2 | A | Q | Q | Q | Q | Q | Q |
| 40 | 40 | Fr2 | R | A | A | A | A | A | A |
| 41 | 41 | Fr2 | P | P | P | P | P | P | P |
| 42 | 42 | Fr2 | G | G | G | G | G | G | G |
| 43 | 43 | Fr2 | Q | Q | Q | Q | Q | Q | Q |
| 44 | 44 | Fr2 | G | G | G | G | G | G | G |
| 45 | 45 | Fr2 | L | L | L | L | L | L | L |
| 46 | 46 | Fr2 | E | E | E | E | E | E | E |
| 47 | 47 | Fr2 | W | W | W | W | W | W | W |
| 48 | 48 | Fr2 | I | M | I | I | I | I | I |
| 49 | 49 | Fr2 | G | G | G | G | G | G | G |
| 50 | 50 | CDR-H2 | A | G | A | A | A | A | A |
| 51 | 51 | CDR-H2 | T | I | T | T | T | T | T |
| 52 | 52 | CDR-H2 | N | I | N | N | N | N | N |
| 52A | 53 | CDR-H2 | P | P | P | P | P | P | P |
| 52B | | CDR-H2 | _ | _ | _ | _ | _ | _ | _ |
| 52C | | CDR-H2 | _ | _ | _ | _ | _ | _ | _ |
| 53 | 54 | CDR-H2 | N | I | N | N | N | N | N |
| 54 | 55 | CDR-H2 | N | F | N | N | N | N | N |
| 55 | 56 | CDR-H2 | G | G | G | G | G | G | G |
| 56 | 57 | CDR-H2 | Y | T | Y | Y | Y | Y | Y |
| 57 | 58 | CDR-H2 | T | T | T | T | T | T | T |
| 58 | 59 | CDR-H2 | D | T | D | D | D | D | D |
| 59 | 60 | CDR-H2 | Y | Y | Y | Y | Y | Y | Y |
| 60 | 61 | CDR-H2 | N | A | N | N | N | N | N |
| 61 | 62 | CDR-H2 | Q | Q | Q | Q | Q | Q | Q |
| 62 | 63 | CDR-H2 | R | K | R | R | R | R | R |
| 63 | 64 | CDR-H2 | F | F | F | F | F | F | F |

FIG. 10C

| Humanized 5C1 Vh Regions | | | | | | | | | |
|---|---|---|---|---|---|---|---|---|---|
| Kabat # | Linear # | FR or CDR | Murine 5C1 (SEQ ID NO: 9) | Hu VH Acceptor FR (SEQ ID NO: 13) | 5C1 H1 (SEQ ID NO: 14) | 5C1 H2 (SEQ ID NO: 15) | 5C1 H3 (SEQ ID NO: 16) | 5C1 H4 (SEQ ID NO: 17) | 5C1 H5 (SEQ ID NO: 18) |
| 64 | 65 | CDR-H2 | K | Q | K | K | K | K | K |
| 65 | 66 | CDR-H2 | D | G | D | D | D | D | D |
| 66 | 67 | Fr3 | K | R | R | R | R | R | R |
| 67 | 68 | Fr3 | A | V | A | V | A | A | V |
| 68 | 69 | Fr3 | I | T | T | T | T | T | T |
| 69 | 70 | Fr3 | L | I | L | I | L | L | I |
| 70 | 71 | Fr3 | T | T | T | T | T | T | T |
| 71 | 72 | Fr3 | A | A | A | A | A | A | A |
| 72 | 73 | Fr3 | D | D | D | D | D | D | D |
| 73 | 74 | Fr3 | K | E | K | K | K | K | K |
| 74 | 75 | Fr3 | S | S | S | S | S | S | S |
| 75 | 76 | Fr3 | S | T | T | T | T | T | T |
| 76 | 77 | Fr3 | N | N | N | N | N | N | N |
| 77 | 78 | Fr3 | T | T | T | T | T | T | T |
| 78 | 79 | Fr3 | A | A | A | A | A | A | A |
| 79 | 80 | Fr3 | Y | Y | Y | Y | Y | Y | Y |
| 80 | 81 | Fr3 | M | M | M | M | M | M | M |
| 81 | 82 | Fr3 | H | E | E | E | E | E | E |
| 82 | 83 | Fr3 | L | L | L | L | L | L | L |
| 82A | 84 | Fr3 | S | S | S | S | S | S | S |
| 82B | 85 | Fr3 | S | S | S | S | S | S | S |
| 82C | 86 | Fr3 | L | L | L | L | L | L | L |
| 83 | 87 | Fr3 | T | R | R | R | R | R | R |
| 84 | 88 | Fr3 | S | S | S | S | S | S | S |
| 85 | 89 | Fr3 | E | E | E | E | E | E | E |
| 86 | 90 | Fr3 | D | D | D | D | D | D | D |
| 87 | 91 | Fr3 | S | T | T | T | T | T | T |
| 88 | 92 | Fr3 | A | A | A | A | A | A | A |
| 89 | 93 | Fr3 | V | V | V | V | V | V | V |
| 90 | 94 | Fr3 | Y | Y | Y | Y | Y | Y | Y |
| 91 | 95 | Fr3 | F | Y | Y | Y | F | Y | Y |
| 92 | 96 | Fr3 | C | C | C | C | C | C | C |
| 93 | 97 | Fr3 | A | A | A | A | A | A | A |
| 94 | 98 | Fr3 | S | R | R | R | S | S | S |
| 95 | 99 | CDR-H3 | G | E | G | G | G | G | G |

FIG. 10D

| Humanized 5C1 Vh Regions | | | | | | | | | |
|---|---|---|---|---|---|---|---|---|---|
| Kabat # | Linear # | FR or CDR | Murine 5C1 (SEQ ID NO: 9) | Hu VH Acceptor FR (SEQ ID NO: 13) | 5C1 H1 (SEQ ID NO: 14) | 5C1 H2 (SEQ ID NO: 15) | 5C1 H3 (SEQ ID NO: 16) | 5C1 H4 (SEQ ID NO: 17) | 5C1 H5 (SEQ ID NO: 18) |
| 96 | 100 | CDR-H3 | G | G | G | G | G | G | G |
| 97 | 101 | CDR-H3 | H | N | H | H | H | H | H |
| 98 | | CDR-H3 | _ | L | _ | _ | _ | _ | _ |
| 99 | | CDR-H3 | _ | N | _ | _ | _ | _ | _ |
| 100 | | CDR-H3 | _ | W | _ | _ | _ | _ | _ |
| 100A | 102 | CDR-H3 | L | L | L | L | L | L | L |
| 100B | | CDR-H3 | _ | _ | _ | _ | _ | _ | _ |
| 100C | | CDR-H3 | _ | _ | _ | _ | _ | _ | _ |
| 100D | | CDR-H3 | _ | _ | _ | _ | _ | _ | _ |
| 100E | | CDR-H3 | _ | _ | _ | _ | _ | _ | _ |
| 100F | | CDR-H3 | _ | _ | _ | _ | _ | _ | _ |
| 100G | | CDR-H3 | _ | _ | _ | _ | _ | _ | _ |
| 100H | | CDR-H3 | _ | _ | _ | _ | _ | _ | _ |
| 100I | | CDR-H3 | _ | _ | _ | _ | _ | _ | _ |
| 100J | | CDR-H3 | _ | _ | _ | _ | _ | _ | _ |
| 100K | | CDR-H3 | _ | _ | _ | _ | _ | _ | _ |
| 101 | 103 | CDR-H3 | A | D | A | A | A | A | A |
| 102 | 104 | CDR-H3 | Y | P | Y | Y | Y | Y | Y |
| 103 | 105 | Fr4 | W | W | W | W | W | W | W |
| 104 | 106 | Fr4 | G | G | G | G | G | G | G |
| 105 | 107 | Fr4 | Q | Q | Q | Q | Q | Q | Q |
| 106 | 108 | Fr4 | G | G | G | G | G | G | G |
| 107 | 109 | Fr4 | T | T | T | T | T | T | T |
| 108 | 110 | Fr4 | V | L | L | L | L | L | L |
| 109 | 111 | Fr4 | V | V | V | V | V | V | V |
| 110 | 112 | Fr4 | T | T | T | T | T | T | T |
| 111 | 113 | Fr4 | V | V | V | V | V | V | V |
| 112 | 114 | Fr4 | S | S | S | S | S | S | S |
| 113 | 115 | Fr4 | A | S | S | S | S | S | S |

FIG. 11A

| Humanized 5C1 Vk Regions | | | | | | | | |
|---|---|---|---|---|---|---|---|---|
| Kabat # | Linear # | FR or CDR | Murine 5C1 VL (SEQ ID NO: 24) | Hu Vk Acceptor Fr (SEQ ID NO: 28) | 5C1 L1 (SEQ ID NO:29 ) | 5C1 L2 (SEQ ID NO: 30) | 5C1 L3 (SEQ ID NO: 31) | 5C1 L4 (SEQ ID NO: 32) |
| | | | | Acc# CAB51293.1 | | | | |
| 1 | 1 | Fr1 | D | D | D | D | D | D |
| 2 | 2 | Fr1 | V | I | V | I | V | I |
| 3 | 3 | Fr1 | V | V | V | V | V | V |
| 4 | 4 | Fr1 | M | M | M | M | M | M |
| 5 | 5 | Fr1 | T | T | T | T | T | T |
| 6 | 6 | Fr1 | Q | Q | Q | Q | Q | Q |
| 7 | 7 | Fr1 | I | S | S | S | S | S |
| 8 | 8 | Fr1 | P | P | P | P | P | P |
| 9 | 9 | Fr1 | L | L | L | L | L | L |
| 10 | 10 | Fr1 | Y | S | S | S | S | S |
| 11 | 11 | Fr1 | L | L | L | L | L | L |
| 12 | 12 | Fr1 | S | P | S | S | S | S |
| 13 | 13 | Fr1 | V | V | V | V | V | V |
| 14 | 14 | Fr1 | S | T | S | S | S | S |
| 15 | 15 | Fr1 | P | P | P | P | P | P |
| 16 | 16 | Fr1 | G | G | G | G | G | G |
| 17 | 17 | Fr1 | D | E | E | E | E | E |
| 18 | 18 | Fr1 | Q | P | P | P | P | P |
| 19 | 19 | Fr1 | A | A | A | A | A | A |
| 20 | 20 | Fr1 | S | S | S | S | S | S |
| 21 | 21 | Fr1 | I | I | I | I | I | I |
| 22 | 22 | Fr1 | S | S | S | S | S | S |
| 23 | 23 | Fr1 | C | C | C | C | C | C |
| 24 | 24 | CDR-L1 | R | R | R | R | R | R |
| 25 | 25 | CDR-L1 | S | S | S | S | S | S |
| 26 | 26 | CDR-L1 | S | S | S | S | S | S |
| 27 | 27 | CDR-L1 | Q | Q | Q | Q | Q | Q |
| 27A | 28 | CDR-L1 | S | S | S | S | S | S |
| 27B | 29 | CDR-L1 | L | L | L | L | L | L |
| 27C | 30 | CDR-L1 | F | L | F | F | F | F |
| 27D | 31 | CDR-L1 | H | H | H | H | H | H |

FIG. 11B

| Humanized 5C1 Vk Regions | | | | | | | | |
|---|---|---|---|---|---|---|---|---|
| Kabat # | Linear # | FR or CDR | Murine 5C1 VL (SEQ ID NO: 24) | Hu Vk Acceptor Fr (SEQ ID NO: 28) | 5C1 L1 (SEQ ID NO:29 ) | 5C1 L2 (SEQ ID NO: 30) | 5C1 L3 (SEQ ID NO: 31) | 5C1 L4 (SEQ ID NO: 32) |
| 27E | 32 | CDR-L1 | S | S | S | S | S | S |
| 27F | | CDR-L1 | _ | _ | _ | _ | _ | _ |
| 28 | 33 | CDR-L1 | K | N | K | K | K | K |
| 29 | 34 | CDR-L1 | G | G | G | G | G | G |
| 30 | 35 | CDR-L1 | N | Y | N | N | N | N |
| 31 | 36 | CDR-L1 | T | N | T | T | T | T |
| 32 | 37 | CDR-L1 | Y | Y | Y | Y | Y | Y |
| 33 | 38 | CDR-L1 | L | L | L | L | L | L |
| 34 | 39 | CDR-L1 | H | D | H | H | H | H |
| 35 | 40 | Fr2 | W | W | W | W | W | W |
| 36 | 41 | Fr2 | Y | Y | Y | Y | Y | Y |
| 37 | 42 | Fr2 | L | L | L | L | L | L |
| 38 | 43 | Fr2 | Q | Q | Q | Q | Q | Q |
| 39 | 44 | Fr2 | K | K | K | K | K | K |
| 40 | 45 | Fr2 | P | P | P | P | P | P |
| 41 | 46 | Fr2 | G | G | G | G | G | G |
| 42 | 47 | Fr2 | Q | Q | Q | Q | Q | Q |
| 43 | 48 | Fr2 | S | S | S | S | S | S |
| 44 | 49 | Fr2 | P | P | P | P | P | P |
| 45 | 50 | Fr2 | K | Q | K | K | Q | Q |
| 46 | 51 | Fr2 | L | L | L | L | L | L |
| 47 | 52 | Fr2 | L | L | L | L | L | L |
| 48 | 53 | Fr2 | I | I | I | I | I | I |
| 49 | 54 | Fr2 | N | Y | N | Y | N | Y |
| 50 | 55 | CDR-L2 | R | L | R | R | R | R |
| 51 | 56 | CDR-L2 | V | G | V | V | V | V |
| 52 | 57 | CDR-L2 | S | S | S | S | S | S |
| 53 | 58 | CDR-L2 | N | N | N | N | N | N |
| 54 | 59 | CDR-L2 | R | R | R | R | R | R |
| 55 | 60 | CDR-L2 | F | A | F | F | F | F |
| 56 | 61 | CDR-L2 | S | S | S | S | S | S |
| 57 | 62 | Fr3 | G | G | G | G | G | G |
| 58 | 63 | Fr3 | V | V | V | V | V | V |
| 59 | 64 | Fr3 | P | P | P | P | P | P |
| 60 | 65 | Fr3 | D | D | D | D | D | D |

FIG. 11C

| Humanized 5C1 Vk Regions | | | | | | | | |
|---|---|---|---|---|---|---|---|---|
| Kabat # | Linear # | FR or CDR | Murine 5C1 VL (SEQ ID NO: 24) | Hu Vk Acceptor Fr (SEQ ID NO: 28) | 5C1 L1 (SEQ ID NO:29 ) | 5C1 L2 (SEQ ID NO: 30) | 5C1 L3 (SEQ ID NO: 31) | 5C1 L4 (SEQ ID NO: 32) |
| 61 | 66 | Fr3 | R | R | R | R | R | R |
| 62 | 67 | Fr3 | F | F | F | F | F | F |
| 63 | 68 | Fr3 | S | S | S | S | S | S |
| 64 | 69 | Fr3 | G | G | G | G | G | G |
| 65 | 70 | Fr3 | S | S | S | S | S | S |
| 66 | 71 | Fr3 | G | G | G | G | G | G |
| 67 | 72 | Fr3 | S | S | S | S | S | S |
| 68 | 73 | Fr3 | G | G | G | G | G | G |
| 69 | 74 | Fr3 | T | T | T | T | T | T |
| 70 | 75 | Fr3 | D | D | D | D | D | D |
| 71 | 76 | Fr3 | F | F | F | F | F | F |
| 72 | 77 | Fr3 | T | T | T | T | T | T |
| 73 | 78 | Fr3 | L | L | L | L | L | L |
| 74 | 79 | Fr3 | K | K | K | K | K | K |
| 75 | 80 | Fr3 | I | I | I | I | I | I |
| 76 | 81 | Fr3 | S | S | S | S | S | S |
| 77 | 82 | Fr3 | G | R | R | R | R | R |
| 78 | 83 | Fr3 | V | V | V | V | V | V |
| 79 | 84 | Fr3 | E | E | E | E | E | E |
| 80 | 85 | Fr3 | A | A | A | A | A | A |
| 81 | 86 | Fr3 | E | E | E | E | E | E |
| 82 | 87 | Fr3 | D | D | D | D | D | D |
| 83 | 88 | Fr3 | L | V | V | V | V | V |
| 84 | 89 | Fr3 | G | G | G | G | G | G |
| 85 | 90 | Fr3 | V | V | V | V | V | V |
| 86 | 91 | Fr3 | Y | Y | Y | Y | Y | Y |
| 87 | 92 | Fr3 | F | Y | F | Y | F | Y |
| 88 | 93 | Fr3 | C | C | C | C | C | C |
| 89 | 94 | CDR-L3 | S | M | S | S | S | S |
| 90 | 95 | CDR-L3 | Q | Q | Q | Q | Q | Q |
| 91 | 96 | CDR-L3 | S | A | S | S | S | S |
| 92 | 97 | CDR-L3 | A | L | A | A | A | A |
| 93 | 98 | CDR-L3 | H | Q | H | H | H | H |
| 94 | 99 | CDR-L3 | V | T | V | V | V | V |
| 95 | 100 | CDR-L3 | P | P | P | P | P | P |

FIG. 11D

| Humanized 5C1 Vk Regions | | | | | | | | |
|---|---|---|---|---|---|---|---|---|
| Kabat # | Linear # | FR or CDR | Murine 5C1 VL (SEQ ID NO: 24) | Hu Vk Acceptor Fr (SEQ ID NO: 28) | 5C1 L1 (SEQ ID NO:29 ) | 5C1 L2 (SEQ ID NO: 30) | 5C1 L3 (SEQ ID NO: 31) | 5C1 L4 (SEQ ID NO: 32) |
| 95A | | CDR-L3 | _ | _ | _ | _ | _ | _ |
| 95B | | CDR-L3 | _ | _ | _ | _ | _ | _ |
| 95C | | CDR-L3 | _ | _ | _ | _ | _ | _ |
| 95D | | CDR-L3 | _ | _ | _ | _ | _ | _ |
| 95E | | CDR-L3 | _ | _ | _ | _ | _ | _ |
| 95F | | CDR-L3 | _ | _ | _ | _ | _ | _ |
| 96 | 101 | CDR-L3 | W | P | W | W | W | W |
| 97 | 102 | CDR-L3 | T | T | T | T | T | T |
| 98 | 103 | Fr4 | F | F | F | F | F | F |
| 99 | 104 | Fr4 | G | G | G | G | G | G |
| 100 | 105 | Fr4 | G | G | G | G | G | G |
| 101 | 106 | Fr4 | G | G | G | G | G | G |
| 102 | 107 | Fr4 | T | T | T | T | T | T |
| 103 | 108 | Fr4 | K | K | K | K | K | K |
| 104 | 109 | Fr4 | L | V | V | V | V | V |
| 105 | 110 | Fr4 | E | E | E | E | E | E |
| 106 | 111 | Fr4 | I | I | I | I | I | I |
| 106A | | Fr4 | _ | _ | _ | _ | _ | _ |
| 107 | 112 | Fr4 | R | K | K | K | K | K |

SEQUENCE LISTING

```
<160> NUMBER OF SEQ ID NOS: 41

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140


<210> SEQ ID NO 2
<211> LENGTH: 35
<212> TYPE: PRT
<213> ORGANISM: Homo sapiens

<400> SEQUENCE: 2

Glu Gln Val Thr Asn Val Gly Gly Ala Val Val Thr Gly Val Thr Ala
```

1 5 10 15

Val Ala Gln Lys Thr Val Glu Gly Ala Gly Ser Ile Ala Ala Ala Thr
20 25 30

Gly Phe Val
35

<210> SEQ ID NO 3
<211> LENGTH: 28
<212> TYPE: PRT
<213> ORGANISM: Homo sapiens

<400> SEQUENCE: 3

Lys Glu Gln Val Thr Asn Val Gly Gly Ala Val Val Thr Gly Val Thr
1 5 10 15

Ala Val Ala Gln Lys Thr Val Glu Gly Ala Gly Ser
20 25

<210> SEQ ID NO 4
<211> LENGTH: 12
<212> TYPE: PRT
<213> ORGANISM: Homo sapiens

<400> SEQUENCE: 4

Val Asp Pro Asp Asn Glu Ala Tyr Glu Gly Gly Cys
1 5 10

<210> SEQ ID NO 5
<211> LENGTH: 402
<212> TYPE: DNA
<213> ORGANISM: Artificial Sequence
<220> FEATURE:
<223> OTHER INFORMATION: Synthesized

<400> SEQUENCE: 5
atggaaaggc actggatctt tctcttcctg ttatcagtaa ctggaggtgt ccactcccag 60
gtccagctgc agcagtctgg ggctgaactg gcaaaacctg ggacctcagt gcagatgtcc 120
tgcaaggctt ctggctacac ctttactaat tactggatga actggataaa agcgaggcct 180
ggacagggtc tggaatggat tggggctact aatcctaaca atggttatac tgactacaat 240
cagaggttca aggacaaggc catattaact gcagacaaat cctccaatac agcctacatg 300
cacctgagca gcctgacatc tgaagactct gcagtctatt tctgtgcaag tggggggcac 360
ttggcttact ggggccaggg gactgtggtc actgtctctg ca 402

<210> SEQ ID NO 6
<211> LENGTH: 134
<212> TYPE: PRT
<213> ORGANISM: Artificial Sequence
<220> FEATURE:
<223> OTHER INFORMATION: Synthesized

<400> SEQUENCE: 6

Met Glu Arg His Trp Ile Phe Leu Phe Leu Leu Ser Val Thr Gly Gly
1 5 10 15

Val His Ser Gln Val Gln Leu Gln Gln Ser Gly Ala Glu Leu Ala Lys
20 25 30

Pro Gly Thr Ser Val Gln Met Ser Cys Lys Ala Ser Gly Tyr Thr Phe
35 40 45

Thr Asn Tyr Trp Met Asn Trp Ile Lys Ala Arg Pro Gly Gln Gly Leu
50 55 60

-continued

Glu Trp Ile Gly Ala Thr Asn Pro Asn Asn Gly Tyr Thr Asp Tyr Asn
65 70 75 80

Gln Arg Phe Lys Asp Lys Ala Ile Leu Thr Ala Asp Lys Ser Ser Asn
85 90 95

Thr Ala Tyr Met His Leu Ser Ser Leu Thr Ser Glu Asp Ser Ala Val
100 105 110

Tyr Phe Cys Ala Ser Gly Gly His Leu Ala Tyr Trp Gly Gln Gly Thr
115 120 125

Val Val Thr Val Ser Ala
130

<210> SEQ ID NO 7
<211> LENGTH: 393
<212> TYPE: DNA
<213> ORGANISM: Artificial Sequence
<220> FEATURE:
<223> OTHER INFORMATION: Synthesized

<400> SEQUENCE: 7
atgaagttgc ctgttaggct gttggtgctg atgttctgga ttcctgcttc cagcagtgat 60
gttgtgatga cccaaattcc actctacctg tctgtcagtc ctggagatca agcctccatc 120
tcttgcagat ctagtcagag ccttttccat agtaaaggaa acacctattt acattggtat 180
ctgcagaagc caggccagtc tccaaagctc ctgatcaaca gggtttccaa ccgattttct 240
ggggtcccag acaggttcag tggcagtgga tcagggacag atttcacact caagatcagc 300
ggagtggagg ctgaagatct gggagtttat ttctgttctc aaagtgcaca tgttccgtgg 360
acgttcggtg gaggcaccaa gctggaaatc aga 393

<210> SEQ ID NO 8
<211> LENGTH: 131
<212> TYPE: PRT
<213> ORGANISM: Artificial Sequence
<220> FEATURE:
<223> OTHER INFORMATION: Synthesized

<400> SEQUENCE: 8

Met Lys Leu Pro Val Arg Leu Leu Val Leu Met Phe Trp Ile Pro Ala
1 5 10 15

Ser Ser Ser Asp Val Val Met Thr Gln Ile Pro Leu Tyr Leu Ser Val
20 25 30

Ser Pro Gly Asp Gln Ala Ser Ile Ser Cys Arg Ser Ser Gln Ser Leu
35 40 45

Phe His Ser Lys Gly Asn Thr Tyr Leu His Trp Tyr Leu Gln Lys Pro
50 55 60

Gly Gln Ser Pro Lys Leu Leu Ile Asn Arg Val Ser Asn Arg Phe Ser
65 70 75 80

Gly Val Pro Asp Arg Phe Ser Gly Ser Gly Ser Gly Thr Asp Phe Thr
85 90 95

Leu Lys Ile Ser Gly Val Glu Ala Glu Asp Leu Gly Val Tyr Phe Cys
100 105 110

Ser Gln Ser Ala His Val Pro Trp Thr Phe Gly Gly Gly Thr Lys Leu
115 120 125

Glu Ile Arg
130

<210> SEQ ID NO 9
<211> LENGTH: 115

<212> TYPE: PRT
<213> ORGANISM: Artificial Sequence
<220> FEATURE:
<223> OTHER INFORMATION: Synthesized

<400> SEQUENCE: 9

```
Gln Val Gln Leu Gln Gln Ser Gly Ala Glu Leu Ala Lys Pro Gly Thr
 1               5                  10                  15

Ser Val Gln Met Ser Cys Lys Ala Ser Gly Tyr Thr Phe Thr Asn Tyr
            20                  25                  30

Trp Met Asn Trp Ile Lys Ala Arg Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Lys Ala Ile Leu Thr Ala Asp Lys Ser Ser Asn Thr Ala Tyr
65                  70                  75                  80

Met His Leu Ser Ser Leu Thr Ser Glu Asp Ser Ala Val Tyr Phe Cys
                85                  90                  95

Ala Ser Gly Gly His Leu Ala Tyr Trp Gly Gln Gly Thr Val Val Thr
            100                 105                 110

Val Ser Ala
        115
```

<210> SEQ ID NO 10
<211> LENGTH: 5
<212> TYPE: PRT
<213> ORGANISM: Artificial Sequence
<220> FEATURE:
<223> OTHER INFORMATION: Synthesized

<400> SEQUENCE: 10

```
Asn Tyr Trp Met Asn
 1               5
```

<210> SEQ ID NO 11
<211> LENGTH: 17
<212> TYPE: PRT
<213> ORGANISM: Artificial Sequence
<220> FEATURE:
<223> OTHER INFORMATION: Synthesized

<400> SEQUENCE: 11

```
Ala Thr Asn Pro Asn Asn Gly Tyr Thr Asp Tyr Asn Gln Arg Phe Lys
 1               5                  10                  15

Asp
```

<210> SEQ ID NO 12
<211> LENGTH: 6
<212> TYPE: PRT
<213> ORGANISM: Artificial Sequence
<220> FEATURE:
<223> OTHER INFORMATION: Synthesized

<400> SEQUENCE: 12

```
Gly Gly His Leu Ala Tyr
 1               5
```

<210> SEQ ID NO 13
<211> LENGTH: 118
<212> TYPE: PRT
<213> ORGANISM: Artificial Sequence
<220> FEATURE:
<223> OTHER INFORMATION: Synthesized

<400> SEQUENCE: 13

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Asn Asn Tyr
20 25 30

Ala Ile Asn Trp Val Arg Gln Ala Pro Gly Gln Gly Leu Glu Trp Met
35 40 45

Gly Gly Ile Ile Pro Ile Phe Gly Thr Thr Thr Tyr Ala Gln Lys Phe
50 55 60

Gln Gly Arg Val Thr Ile Thr Ala Asp Glu Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Glu Gly Asn Leu Asn Trp Leu Asp Pro Trp Gly Gln Gly Thr
100 105 110

Leu Val Thr Val Ser Ser
115

<210> SEQ ID NO 14
<211> LENGTH: 115
<212> TYPE: PRT
<213> ORGANISM: Artificial Sequence
<220> FEATURE:
<223> OTHER INFORMATION: Synthesized

<400> SEQUENCE: 14

Gln Val Gln Leu Val Gln Ser Gly Ala Glu Leu Lys Lys Pro Gly Ser
1 5 10 15

Ser Val Lys Val Ser Cys Lys Ala Ser Gly Tyr Thr Phe Thr Asn Tyr
20 25 30

Trp Met Asn Trp Val Arg Gln Ala Pro Gly Gln Gly Leu Glu Trp Ile
35 40 45

Gly Ala Thr Asn Pro Asn Asn Gly Tyr Thr Asp Tyr Asn Gln Arg Phe
50 55 60

Lys Asp Arg Ala Thr Leu Thr Ala Asp Lys Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Gly Gly His Leu Ala Tyr Trp Gly Gln Gly Thr Leu Val Thr
100 105 110

Val Ser Ser
115

<210> SEQ ID NO 15
<211> LENGTH: 115
<212> TYPE: PRT
<213> ORGANISM: Artificial Sequence
<220> FEATURE:
<223> OTHER INFORMATION: Synthesized

<400> SEQUENCE: 15

Gln Val Gln Leu Val Gln Ser Gly Ala Glu Leu Lys Lys Pro Gly Ser
1 5 10 15

Ser Val Lys Val Ser Cys Lys Ala Ser Gly Tyr Thr Phe Thr Asn Tyr
20 25 30

Trp Met Asn Trp Val Arg Gln Ala Pro Gly Gln Gly Leu Glu Trp Ile
35 40 45

Gly Ala Thr Asn Pro Asn Asn Gly Tyr Thr Asp Tyr Asn Gln Arg Phe
50 55 60

Lys Asp Arg Val Thr Ile Thr Ala Asp Lys Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Gly Gly His Leu Ala Tyr Trp Gly Gln Gly Thr Leu Val Thr
100 105 110

Val Ser Ser
115

<210> SEQ ID NO 16
<211> LENGTH: 115
<212> TYPE: PRT
<213> ORGANISM: Artificial Sequence
<220> FEATURE:
<223> OTHER INFORMATION: Synthesized

<400> SEQUENCE: 16

Gln Val Gln Leu Val Gln Ser Gly Ala Glu Leu Lys Lys Pro Gly Ser
1 5 10 15

Ser Val Lys Val Ser Cys Lys Ala Ser Gly Tyr Thr Phe Thr Asn Tyr
20 25 30

Trp Met Asn Trp Val Arg Gln Ala Pro Gly Gln Gly Leu Glu Trp Ile
35 40 45

Gly Ala Thr Asn Pro Asn Asn Gly Tyr Thr Asp Tyr Asn Gln Arg Phe
50 55 60

Lys Asp Arg Ala Thr Leu Thr Ala Asp Lys Ser Thr Asn Thr Ala Tyr
65 70 75 80

Met Glu Leu Ser Ser Leu Arg Ser Glu Asp Thr Ala Val Tyr Phe Cys
85 90 95

Ala Ser Gly Gly His Leu Ala Tyr Trp Gly Gln Gly Thr Leu Val Thr
100 105 110

Val Ser Ser
115

<210> SEQ ID NO 17
<211> LENGTH: 115
<212> TYPE: PRT
<213> ORGANISM: Artificial Sequence
<220> FEATURE:
<223> OTHER INFORMATION: Synthesized

<400> SEQUENCE: 17

Gln Val Gln Leu Val Gln Ser Gly Ala Glu Leu Lys Lys Pro Gly Ser
1 5 10 15

Ser Val Lys Val Ser Cys Lys Ala Ser Gly Tyr Thr Phe Thr Asn Tyr
20 25 30

Trp Met Asn Trp Val Arg Gln Ala Pro Gly Gln Gly Leu Glu Trp Ile
35 40 45

Gly Ala Thr Asn Pro Asn Asn Gly Tyr Thr Asp Tyr Asn Gln Arg Phe
50 55 60

Lys Asp Arg Ala Thr Leu Thr Ala Asp Lys Ser Thr Asn Thr Ala Tyr
65 70 75 80

Met Glu Leu Ser Ser Leu Arg Ser Glu Asp Thr Ala Val Tyr Tyr Cys
85 90 95

Ala Ser Gly Gly His Leu Ala Tyr Trp Gly Gln Gly Thr Leu Val Thr

```
            100                 105                 110

Val Ser Ser
        115


<210> SEQ ID NO 18
<211> LENGTH: 115
<212> TYPE: PRT
<213> ORGANISM: Artificial Sequence
<220> FEATURE:
<223> OTHER INFORMATION: Synthesized

<400> SEQUENCE: 18

Gln Val Gln Leu Val Gln Ser Gly Ala Glu Leu Lys Lys Pro Gly Ser
 1               5                  10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser
        115


<210> SEQ ID NO 19
<211> LENGTH: 402
<212> TYPE: DNA
<213> ORGANISM: Artificial Sequence
<220> FEATURE:
<223> OTHER INFORMATION: Synthesized

<400> SEQUENCE: 19

atggagttcg gcctgtcctg gctgttcctg gtggccatcc tgaagggcgt gcagtgccag      60

gtgcagctgg tgcagtccgg cgccgagctg aagaagcccg gctcctccgt gaaggtgtcc     120

tgcaaggcct ccggctacac cttcaccaac tactggatga actgggtgcg ccaggccccc     180

ggccagggcc tggagtggat cggcgccacc aaccccaaca acggctacac cgactacaac     240

cagcgcttca aggaccgcgc caccctgacc gccgacaagt ccaccaacac cgcctacatg     300

gagctgtcct ccctgcgctc cgaggacacc gccgtgtact actgcgcccg cggcggccac     360

ctggcctact ggggccaggg caccctggtg accgtgtcct cc                        402


<210> SEQ ID NO 20
<211> LENGTH: 402
<212> TYPE: DNA
<213> ORGANISM: Artificial Sequence
<220> FEATURE:
<223> OTHER INFORMATION: Synthesized

<400> SEQUENCE: 20

atggagttcg gcctgtcctg gctgttcctg gtggccatcc tgaagggcgt gcagtgccag      60

gtgcagctgg tgcagtccgg cgccgagctg aagaagcccg gctcctccgt gaaggtgtcc     120

tgcaaggcct ccggctacac cttcaccaac tactggatga actgggtgcg ccaggccccc     180
```

ggccagggcc tggagtggat cggcgccacc aaccccaaca acggctacac cgactacaac 240
cagcgcttca aggaccgcgt gaccatcacc gccgacaagt ccaccaacac cgcctacatg 300
gagctgtcct ccctgcgctc cgaggacacc gccgtgtact actgcgcccg cggcggccac 360
ctggcctact ggggccaggg caccctggtg accgtgtcct cc 402

<210> SEQ ID NO 21
<211> LENGTH: 402
<212> TYPE: DNA
<213> ORGANISM: Artificial Sequence
<220> FEATURE:
<223> OTHER INFORMATION: Synthesized

<400> SEQUENCE: 21
atggagttcg gcctgtcctg gctgttcctg gtggccatcc tgaagggcgt gcagtgccag 60
gtgcagctgg tgcagtccgg cgccgagctg aagaagcccg gctcctccgt gaaggtgtcc 120
tgcaaggcct ccggctacac cttcaccaac tactggatga actgggtgcg ccaggccccc 180
ggccagggcc tggagtggat cggcgccacc aaccccaaca acggctacac cgactacaac 240
cagcgcttca aggaccgcgc caccctgacc gccgacaagt ccaccaacac cgcctacatg 300
gagctgtcct ccctgcgctc cgaggacacc gccgtgtact tctgcgcctc cggcggccac 360
ctggcctact ggggccaggg caccctggtg accgtgtcct cc 402

<210> SEQ ID NO 22
<211> LENGTH: 402
<212> TYPE: DNA
<213> ORGANISM: Artificial Sequence
<220> FEATURE:
<223> OTHER INFORMATION: Synthesized

<400> SEQUENCE: 22
atggagttcg gcctgtcctg gctgttcctg gtggccatcc tgaagggcgt gcagtgccag 60
gtgcagctgg tgcagtccgg cgccgagctg aagaagcccg gctcctccgt gaaggtgtcc 120
tgcaaggcct ccggctacac cttcaccaac tactggatga actgggtgcg ccaggccccc 180
ggccagggcc tggagtggat cggcgccacc aaccccaaca acggctacac cgactacaac 240
cagcgcttca aggaccgcgc caccctgacc gccgacaagt ccaccaacac cgcctacatg 300
gagctgtcct ccctgcgctc cgaggacacc gccgtgtact actgcgcctc cggcggccac 360
ctggcctact ggggccaggg caccctggtg accgtgtcct cc 402

<210> SEQ ID NO 23
<211> LENGTH: 402
<212> TYPE: DNA
<213> ORGANISM: Artificial Sequence
<220> FEATURE:
<223> OTHER INFORMATION: Synthesized

<400> SEQUENCE: 23
atggagttcg gcctgtcctg gctgttcctg gtggccatcc tgaagggcgt gcagtgccag 60
gtgcagctgg tgcagtccgg cgccgagctg aagaagcccg gctcctccgt gaaggtgtcc 120
tgcaaggcct ccggctacac cttcaccaac tactggatga actgggtgcg ccaggccccc 180
ggccagggcc tggagtggat cggcgccacc aaccccaaca acggctacac cgactacaac 240
cagcgcttca aggaccgcgt gaccatcacc gccgacaagt ccaccaacac cgcctacatg 300
gagctgtcct ccctgcgctc cgaggacacc gccgtgtact actgcgccag cggcggccac 360
ctggcctact ggggccaggg caccctggtg accgtgtcct cc 402

<210> SEQ ID NO 24
<211> LENGTH: 112
<212> TYPE: PRT
<213> ORGANISM: Artificial Sequence
<220> FEATURE:
<223> OTHER INFORMATION: Synthesized

<400> SEQUENCE: 24

```
Asp Val Val Met Thr Gln Ile Pro Leu Tyr Leu Ser Val Ser Pro Gly
 1               5                  10                  15

Asp Gln Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Lys Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Arg
            100                 105                 110
```

<210> SEQ ID NO 25
<211> LENGTH: 16
<212> TYPE: PRT
<213> ORGANISM: Artificial Sequence
<220> FEATURE:
<223> OTHER INFORMATION: Synthesized

<400> SEQUENCE: 25

```
Arg Ser Ser Gln Ser Leu Phe His Ser Lys Gly Asn Thr Tyr Leu His
 1               5                  10                  15
```

<210> SEQ ID NO 26
<211> LENGTH: 7
<212> TYPE: PRT
<213> ORGANISM: Artificial Sequence
<220> FEATURE:
<223> OTHER INFORMATION: Synthesized

<400> SEQUENCE: 26

```
Arg Val Ser Asn Arg Phe Ser
 1               5
```

<210> SEQ ID NO 27
<211> LENGTH: 9
<212> TYPE: PRT
<213> ORGANISM: Artificial Sequence
<220> FEATURE:
<223> OTHER INFORMATION: Synthesized

<400> SEQUENCE: 27

```
Ser Gln Ser Ala His Val Pro Trp Thr
 1               5
```

<210> SEQ ID NO 28
<211> LENGTH: 112
<212> TYPE: PRT
<213> ORGANISM: Artificial Sequence
<220> FEATURE:
<223> OTHER INFORMATION: Synthesized

<400> SEQUENCE: 28

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Ala
85 90 95

Leu Gln Thr Pro Pro Thr Phe Gly Gly Gly Thr Lys Val Glu Ile Lys
100 105 110

<210> SEQ ID NO 29
<211> LENGTH: 112
<212> TYPE: PRT
<213> ORGANISM: Artificial Sequence
<220> FEATURE:
<223> OTHER INFORMATION: Synthesized

<400> SEQUENCE: 29

Asp Val Val Met Thr Gln Ser Pro Leu Ser Leu Ser Val Ser Pro Gly
1 5 10 15

Glu Pro Ala Ser Ile Ser Cys Arg Ser Ser Gln Ser Leu Phe His Ser
20 25 30

Lys Gly Asn Thr Tyr Leu His Trp Tyr Leu Gln Lys Pro Gly Gln Ser
35 40 45

Pro Lys Leu Leu Ile Asn Arg Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Ser Gln Ser
85 90 95

Ala His Val Pro Trp Thr Phe Gly Gly Gly Thr Lys Val Glu Ile Lys
100 105 110

<210> SEQ ID NO 30
<211> LENGTH: 112
<212> TYPE: PRT
<213> ORGANISM: Artificial Sequence
<220> FEATURE:
<223> OTHER INFORMATION: Synthesized

<400> SEQUENCE: 30

Asp Ile Val Met Thr Gln Ser Pro Leu Ser Leu Ser Val Ser Pro Gly
1 5 10 15

Glu Pro Ala Ser Ile Ser Cys Arg Ser Ser Gln Ser Leu Phe His Ser
20 25 30

Lys Gly Asn Thr Tyr Leu His Trp Tyr Leu Gln Lys Pro Gly Gln Ser
35 40 45

Pro Lys Leu Leu Ile Tyr Arg Val Ser Asn Arg Phe Ser Gly Val Pro
50 55 60

Asp Arg Phe Ser Gly Ser Gly Ser Gly Thr Asp Phe Thr Leu Lys Ile
65 70 75 80

```
Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
            100                 105                 110


<210> SEQ ID NO 31
<211> LENGTH: 112
<212> TYPE: PRT
<213> ORGANISM: Artificial Sequence
<220> FEATURE:
<223> OTHER INFORMATION: Synthesized

<400> SEQUENCE: 31

Asp Val Val Met Thr Gln Ser Pro Leu Ser Leu Ser Val Ser Pro Gly
 1               5                  10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Gln Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
            100                 105                 110


<210> SEQ ID NO 32
<211> LENGTH: 112
<212> TYPE: PRT
<213> ORGANISM: Artificial Sequence
<220> FEATURE:
<223> OTHER INFORMATION: Synthesized

<400> SEQUENCE: 32

Asp Ile Val Met Thr Gln Ser Pro Leu Ser Leu Ser Val Ser Pro Gly
 1               5                  10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
            100                 105                 110


<210> SEQ ID NO 33
<211> LENGTH: 402
<212> TYPE: DNA
<213> ORGANISM: Artificial Sequence
<220> FEATURE:
<223> OTHER INFORMATION: Synthesized

<400> SEQUENCE: 33

atggacatgc gcgtgcccgc ccagctgctg ggcctgctga tgctgtgggt gtccggctcc      60
```

tccggcgacg tggtgatgac ccagtccccc ctgtccctgt ccgtgtcccc cggcgagccc 120
gcctccatct cctgccgctc ctcccagtcc ctgttccact ccaagggcaa cacctacctg 180
cactggtacc tgcagaagcc cggccagtcc cccaagctgc tgatcaaccg cgtgtccaac 240
cgcttctccg gcgtgcccga ccgcttctcc ggctccggct ccggcaccga cttcaccctg 300
aagatctccc gcgtggaggc cgaggacgtg ggcgtgtact tctgctccca gtccgcccac 360
gtgccctgga ccttcggcgg cggcaccaag gtggagatca ag 402

<210> SEQ ID NO 34
<211> LENGTH: 402
<212> TYPE: DNA
<213> ORGANISM: Artificial Sequence
<220> FEATURE:
<223> OTHER INFORMATION: Synthesized

<400> SEQUENCE: 34
atggacatgc gcgtgcccgc ccagctgctg ggcctgctga tgctgtgggt gtccggctcc 60
tccggcgaca tcgtgatgac ccagtccccc ctgtccctgt ccgtgtcccc cggcgagccc 120
gcctccatct cctgccgctc ctcccagtcc ctgttccact ccaagggcaa cacctacctg 180
cactggtacc tgcagaagcc cggccagtcc cccaagctgc tgatctaccg cgtgtccaac 240
cgcttctccg gcgtgcccga ccgcttctcc ggctccggct ccggcaccga cttcaccctg 300
aagatctccc gcgtggaggc cgaggacgtg ggcgtgtact actgctccca gtccgcccac 360
gtgccctgga ccttcggcgg cggcaccaag gtggagatca ag 402

<210> SEQ ID NO 35
<211> LENGTH: 402
<212> TYPE: DNA
<213> ORGANISM: Artificial Sequence
<220> FEATURE:
<223> OTHER INFORMATION: Synthesized

<400> SEQUENCE: 35
atggacatgc gcgtgcccgc ccagctgctg ggcctgctga tgctgtgggt gtccggctcc 60
tccggcgacg tggtgatgac ccagtccccc ctgtccctgt ccgtgtcccc cggcgagccc 120
gcctccatct cctgccgctc ctcccagtcc ctgttccact ccaagggcaa cacctacctg 180
cactggtacc tgcagaagcc cggccagtcc ccccagctgc tgatcaaccg cgtgtccaac 240
cgcttctccg gcgtgcccga ccgcttctcc ggctccggct ccggcaccga cttcaccctg 300
aagatctccc gcgtggaggc cgaggacgtg ggcgtgtact tctgctccca gtccgcccac 360
gtgccctgga ccttcggcgg cggcaccaag gtggagatca ag 402

<210> SEQ ID NO 36
<211> LENGTH: 402
<212> TYPE: DNA
<213> ORGANISM: Artificial Sequence
<220> FEATURE:
<223> OTHER INFORMATION: Synthesized

<400> SEQUENCE: 36
atggacatgc gcgtgcccgc ccagctgctg ggcctgctga tgctgtgggt gtccggctcc 60
tccggcgaca tcgtgatgac ccagtccccc ctgtccctgt ccgtgtcccc cggcgagccc 120
gcctccatct cctgccgctc ctcccagtcc ctgttccact ccaagggcaa cacctacctg 180
cactggtacc tgcagaagcc cggccagtcc ccccagctgc tgatctaccg cgtgtccaac 240
cgcttctccg gcgtgcccga ccgcttctcc ggctccggct ccggcaccga cttcaccctg 300
aagatctccc gcgtggaggc cgaggacgtg ggcgtgtact actgctccca gtccgcccac 360
gtgccctgga ccttcggcgg cggcaccaag gtggagatca ag 402

<210> SEQ ID NO 37
<211> LENGTH: 991
<212> TYPE: DNA
<213> ORGANISM: Artificial Sequence
<220> FEATURE:
<223> OTHER INFORMATION: Synthesized

<400> SEQUENCE: 37
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
acatctgcaa cgtgaatcac aagcccagca acaccaaggt ggacaagaga gttgagccca 300
aatcttgtga caaaactcac acatgcccac cgtgcccagc acctgaactc ctggggggac 360
cgtcagtctt cctcttcccc ccaaaaccca aggacaccct catgatctcc cggacccctg 420
aggtcacatg cgtggtggtg gacgtgagcc acgaagaccc tgaggtcaag ttcaactggt 480
acgtggacgg cgtggaggtg cataatgtca agacaaagcc gcgggaggag cagtacaaca 540
gcacgtaccg tgtggtcagc gtcctcaccg tcctgcacca ggactggctg aatggcaagg 600
agtacaagtg caaggtctcc aacaaagccc tcccagcccc catcgagaaa accatctcca 660
aagccaaagg gcagccccga gaaccacagg tgtacacgct gcccccatcc cgggaggaga 720
tgaccaagaa ccaggtcagc ctgacctgcc tggtcaaagg cttctatccc agcgacatcg 780
cgtggagtgg gagagcaatg ggcagccgga gaacaactac aagaccacgc ctcccgtgct 840
ggactccgac ggctccttct tcctctatag caagctcacc gtggacaaga gcaggtggca 900
gcaggggaac gtcttctcat gctccgtgat gcatgaggct ctgcacaacc actacacgca 960
gaagagcctc tccctgtccc cgggtaaatg a 991

<210> SEQ ID NO 38
<211> LENGTH: 330
<212> TYPE: PRT
<213> ORGANISM: Artificial Sequence
<220> FEATURE:
<223> OTHER INFORMATION: Synthesized

<400> SEQUENCE: 38

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys

```
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 39
<211> LENGTH: 321
<212> TYPE: DNA
<213> ORGANISM: Artificial Sequence
<220> FEATURE:
<223> OTHER INFORMATION: Synthesized

<400> SEQUENCE: 39

actgtggctg caccatctgt cttcatcttc ccgccatctg atgagcagtt gaaatctgga      60

actgcctctg ttgtgtgcct gctgaataac ttctatccca gagaggccaa agtacagtgg     120

aaggtggata acgccctcca atcgggtaac tcccaggaga gtgtcacaga gcaggacagc     180

aaggacagca cctacagcct cagcagcacc ctgacgctga gcaaagcaga ctacgagaaa     240

cacaaagtct acgcctgcga agtcacccat cagggcctga gctcgcccgt cacaaagagc     300

ttcaacaggg gagagtgtta g                                               321


<210> SEQ ID NO 40
<211> LENGTH: 106
<212> TYPE: PRT
<213> ORGANISM: Artificial Sequence
<220> FEATURE:
<223> OTHER INFORMATION: Synthesized

<400> SEQUENCE: 40

Thr Val Ala Ala Pro Ser Val Phe Ile Phe Pro Pro Ser Asp Glu Gln
 1               5                  10                  15
```

-continued

```
Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 41
<211> LENGTH: 9
<212> TYPE: PRT
<213> ORGANISM: Homo sapiens

<400> SEQUENCE: 41

Val Asp Pro Asp Asn Glu Ala Tyr Glu
 1               5
```

ANTIBODIES RECOGNIZING α-SYNUCLEIN

CROSS-REFERENCE TO RELATED APPLICATION

The present application is a divisional of U.S. application Ser. No. 14/049,169 filed Oct. 8, 2013, which claims the benefit under 35 U.S.C. § 119(e) of U.S. Application Nos. 61/711,204 filed Oct. 8, 2012, 61/719,281 filed Oct. 26, 2012, 61/840,432 filed Jun. 27, 2013 and 61/872,366 filed Aug. 30, 2013, all of which are incorporated by reference in its entirety for all purposes.

SEQUENCE LISTING

This application includes an electronic sequence listing in a file named 492482_SEQLIST.txt created Feb. 1, 2017 and containing 31,796 bytes, which is hereby incorporated by reference in its entirety for all purposes.

BACKGROUND

Synucleinopathies, also known as Lewy body diseases (LBDs), are characterized by degeneration of the dopaminergic system, motor alterations, cognitive impairment, and formation of Lewy bodies (LBs) and/or Lewy neurites. (McKeith et al., Neurology (1996) 47:1113-24). Synucleinopathies include Parkinson's disease (including idiopathic Parkinson's disease), Diffuse Lewy Body Disease (DLBD) also known as Dementia with Lewy Bodies (DLB), Lewy body variant of Alzheimer's disease (LBV), Combined Alzheimer's and Parkinson disease, pure autonomic failure and multiple system atrophy (MSA; e.g., Olivopontocerebellar Atrophy, Striatonigral Degeneration and Shy-Drager Syndrome). Several nonmotor signs and symptoms are thought to be harbingers for synucleinopathies in the prodromal phase of the diseases (i.e., the presymptomatic, subclinical, preclinical, or premotor period). Such early signs include, for example, REM sleep behavior disorder (RBD), loss of smell and constipation (Mahowald et al., Neurology (2010) 75:488-489). Lewy body diseases continue to be a common cause for movement disorders and cognitive deterioration in the aging population (Galasko et al., Arch. Neurol. (1994) 51:888-95).

α-synuclein is part of a large family of proteins including β- and γ-synuclein and synoretin. α-synuclein is expressed in the normal state associated with synapses and is believed to play a role in neural plasticity, learning and memory. Several studies have implicated α-synuclein with a central role in PD pathogenesis. The protein can aggregate to form insoluble fibrils in pathological conditions. For example, synuclein accumulates in LBs (Spillantini et al., Nature (1997) 388:839-40; Takeda et al., J. Pathol. (1998) 152:367-72; Wakabayashi et al., Neurosci. Lett. (1997) 239:45-8). Mutations in the α-synuclein gene co-segregate with rare familial forms of parkinsonism (Kruger et al., Nature Gen. (1998) 18:106-8; Polymeropoulos, et al., Science (1997) 276:2045-7). Over expression of α-synuclein in transgenic mice (Masliah et al., Science (2000) 287:1265-9) and Drosophila (Feany et al., Nature (2000) 404:394-8) mimics several pathological aspects of Lewy body disease. In addition, it has been suggested that soluble oligomers of synuclein may be neurotoxic (Conway et al., Proc Natl Acad Sci USA (2000) 97:571-576; Volles et al., J. Biochem. (2003) 42:7871-7878). The accumulation of α-synuclein with similar morphological and neurological alterations in species and animal models as diverse as humans, mice, and flies suggests that this molecule contributes to the development of Lewy body disease.

SUMMARY OF THE CLAIMED INVENTION

The invention provides a monoclonal antibody having the three light chain CDRs as defined by Kabat and three heavy chain CDRs as defined by Kabat of monoclonal antibody 5C1, provided that each CDR other than CDRH2 can have up to four deletions, insertions or substitutions, and CDRH2 can have up to six deletions, insertions or substitutions. 5C1 is a mouse antibody characterized by a heavy chain variable region having an amino acid sequence comprising SEQ ID NO: 9 and light chain variable region having an amino acid sequence comprising SEQ ID NO: 24. Optionally, the antibody has the three light chain CDRs as defined by Kabat and three heavy chain CDRs as defined by Kabat of monoclonal antibody 5C1. Optionally, the monoclonal antibody is a humanized, chimeric or veneered form of monoclonal antibody 5C1. Optionally, the antibody is an Fab fragment, or single chain Fv. Optionally, the antibody has an isotype of human IgG1. Optionally, the antibody has an isotype of human IgG2 or IgG4 isotype.

The invention provides an antibody comprising a mature heavy chain variable region having an amino acid sequence at least 90% identical to H4 (SEQ ID NO: 17) and a mature light chain variable region having an amino acid sequence at least 90% identical to L3 (SEQ ID NO: 31), wherein the antibody specifically binds to human alpha synuclein. Some such antibodies comprise three Kabat CDRs of SEQ ID NO: 9 and three Kabat CDRs of SEQ ID NO: 24. In some antibodies at least one of positions H11, H27, H30, H48, and H73 is occupied by L, Y, T, I, and K, respectively, and at least one of positions L12 and L14 is occupied by S. In some antibodies positions H11, H27, H30, H48, and H73 are occupied by L, Y, T, I, and K, respectively, and positions L12 and L14 are occupied by S. In some antibodies, at least one of positions H67, H69, H91, and H94 is occupied by A, L, F, and S, respectively. In some antibodies, positions H67, H69, and H94 are occupied by A, L, and S, respectively. In some antibodies, position H94 is occupied by S. In some antibodies, at least one of positions L2, L45, L49, and L87 is occupied by V, K, N, and F, respectively. In some antibodies, positions L2, L49, and L87 are occupied by V, N, and F, respectively. Some antibodies comprise a mature heavy chain variable region having an amino acid sequence at least 95% identical to H4 (SEQ ID NO: 17) and a mature light chain variable region at least 95% identical to L3 (SEQ ID NO: 31). In some antibodies any differences in CDRs of the mature heavy chain variable region and mature light chain variable region from H4 and L3 (SEQ ID NOS: 17 and 31, respectively) reside in positions H60-H65.

Some antibodies comprise the mature heavy chain variable region has an amino acid sequence designated H4 (SEQ ID NO: 17) and the mature light chain variable region has an amino acid sequence designated L3 (SEQ ID NO: 31). Some antibodies comprise the mature heavy chain variable region has an amino acid sequence designated H5 (SEQ ID NO: 18) and the mature light chain variable region has an amino acid sequence designated L3 (SEQ ID NO: 31).

In any of the above antibodies, the antibody can have at least one mutation in the constant region. Optionally, the mutation reduces complement fixation or activation by the constant region. Optionally, the antibody has a mutation at one or more of positions 241, 264, 265, 270, 296, 297, 322, 329 and 331 by EU numbering. Optionally, the antibody has alanine at positions 318, 320 and 322.

In any of the above antibodies, the mature heavy chain variable region can be fused to a heavy chain constant region and the mature light chain constant region can be fused to a light chain constant region.

In any of the above antibodies, the heavy chain constant region can be a mutant form of natural human constant region which has reduced binding to an Fcγ receptor relative to the natural human constant region.

In any of the above antibodies, the heavy chain constant region can be of human IgG1 isotype. In some antibodies the allotype is G1m3. In some antibodies, the allotype is G1m1.

The invention also provides a method of humanizing an antibody, comprising determining the sequences of the heavy and light chain variable regions of a mouse antibody 5C1, synthesizing a nucleic acid encoding a humanized heavy chain comprising CDRs of the mouse antibody heavy chain and a nucleic acid encoding a humanized light chain comprising CDRs of the mouse antibody light chain, expressing the nucleic acids in a host cell to produce a humanized antibody.

The invention also provides a method of producing a humanized, chimeric or veneered form of antibody 5C1, comprising culturing cells transformed with nucleic acids encoding the heavy and light chains of the antibody, so that the cell secrete the antibody; and purifying the antibody from cell culture media.

The invention also provides a method of producing a cell line producing a humanized, chimeric or veneered form of antibody 5C1, comprising introducing a vector encoding heavy and light chains of an antibody and a selectable marker into cells; propagating the cells under conditions to select for cells having increased copy number of the vector; isolating single cells from the selected cells; and banking cells cloned from a single cell selected based on yield of antibody. Some such methods further comprises propagating the cells under selective conditions and screening for cell lines naturally expressing and secreting at least 100 mg/L/$10^6$ cells/24 h.

The invention further provides a pharmaceutical composition comprising any of the above-mentioned antibodies.

The invention further provides a method of treating or effecting prophylaxis of a Lewy body disease comprising administering an effective regime of any of the above-mentioned antibodies and thereby treating or effecting prophylaxis of the disease.

The invention further provides a method of reducing Lewy body formation in a patient having or at risk of a Lewy body disease, comprising administering to the patient an effective amount of any of the above-mentioned antibodies.

The invention further provides a method of treating a patient having or at risk of a Lewy body disease, comprising administering to the patient an effective regime of any of the above-mentioned antibodies. In some methods, the disease is Parkinson's disease. In some methods, the disease is REM sleep behavior disorder (RBD). In some methods, the disease is Dementia with Lewy Bodies (DLB) or multiple system atrophy (MSA). In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides a method of inhibiting synuclein aggregation or reducing Lewy bodies or synuclein aggregates in a patient having or at risk of a Lewy body disease, comprising administering to the patient an effective amount of an antibody as defined by any of the above-mentioned antibodies. In some such methods, the disease is Parkinson's disease. In some methods, decline of cognitive function in the patient is inhibited. In some methods, neuritic and/or axonal alpha synuclein aggregates are reduced. In some methods, neuritic dystrophy in the patient is reduced. In some methods, synaptic and/or dendritic density is preserved. In some methods, the method preserves synaptophysin and/or MAP2 in the patient.

The invention further provides a method of detecting Lewy bodies in a patient having or at risk of a Lewy body disease, comprising administering to the patient an effective amount of any of the above-mentioned antibodies, wherein the antibody binds to Lewy bodies; and detecting bound antibody in the patient. Optionally, the antibody is labeled.

The invention further provides an isolated nucleic acid, a vector or vectors, and host cells suitable for encoding any of the above-mentioned antibodies.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the amino acid sequences of mouse 5C1 heavy chain mature variable region (SEQ ID NO: 9). CDR regions according to Kabat definition are underlined and in bold.

FIG. 2 shows the amino acid sequences of mouse 5C1 light chain mature variable region (SEQ ID NO: 24). CDR regions according to Kabat definition are underlined and in bold.

FIGS. 10A-D show humanized heavy chain sequences of 5H1 antibodies.

FIGS. 11A-D show humanized light chain sequences of 5H1 antibodies.

BRIEF DESCRIPTION OF THE SEQUENCES

Figure 3:
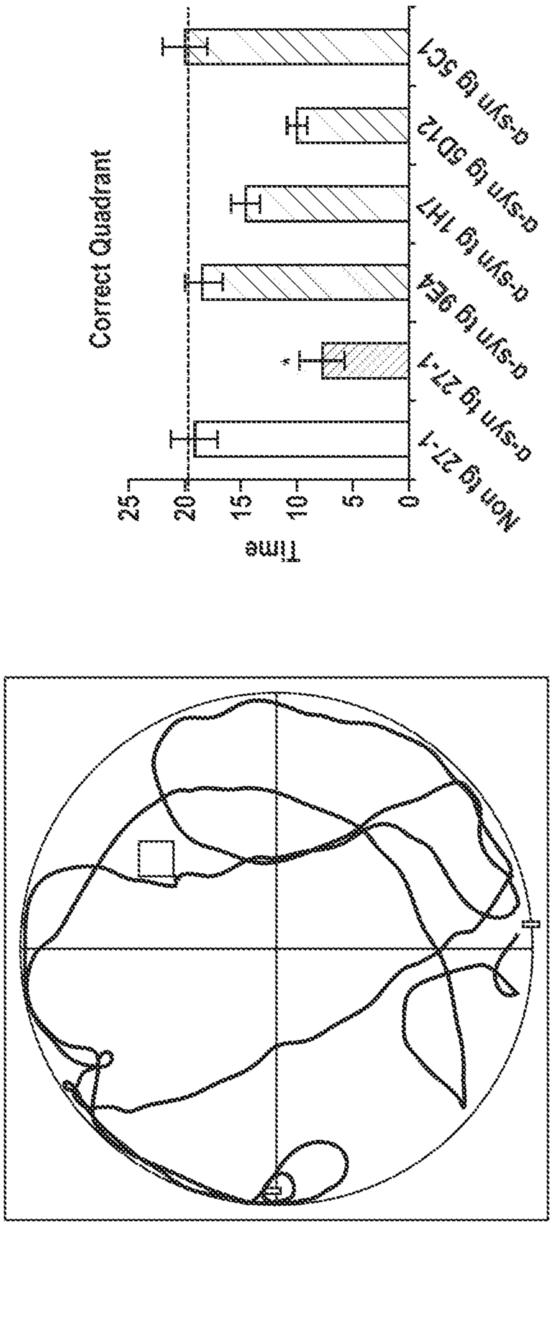
FIG. 3 shows the results of passive immunotherapy with 5C1 on memory performance in probe portion of the Morris water maze test.

SEQ ID NO: 1 is wildtype human α-synuclein.

SEQ ID NO: 2 is the non-amyloid component (NAC) domain of α-synuclein, as reported by Jensen et al. (1995).

SEQ ID NO: 3 is the non-amyloid component (NAC) domain of α-synuclein, as reported by Uéda et al. (1993).

SEQ ID NO: 4 is the 5C1 peptide immunogen amino acid residues 118-129 of human α-synuclein.

(SEQ ID NO: 4)
VDPDNEAYEGGC

SEQ ID NO: 5 is the nucleotide sequence encoding the murine 5C1 heavy chain variable region with sequence encoding signal peptide (underlined).

```
                                          (SEQ ID NO: 5)
ATGGAAAGGCACTGGATCTTTCTCTTCCTGTTATCAGTAACTGGAGGTGT
CCACTCCCAGGTCCAGCTGCAGCAGTCTGGGGCTGAACTGGCAAAACCTG
GGACCTCAGTGCAGATGTCCTGCAAGGCTTCTGGCTACACCTTTACTAAT
TACTGGATGAACTGGATAAAAGCGAGGCCTGGACAGGGTCTGGAATGGAT
TGGGGCTACTAATCCTAACAATGGTTATACTGACTACAATCAGAGGTTCA
AGGACAAGGCCATATTAACTGCAGACAAATCCTCCAATACAGCCTACATG
CACCTGAGCAGCCTGACATCTGAAGACTCTGCAGTCTATTTCTGTGCAAG
TGGGGGGCACTTGGCTTACTGGGGCCAGGGGACTGTGGTCACTGTCTCTG
CA
```

SEQ ID NO: 6 is the murine 5C1 heavy chain variable region with signal peptide (underlined).

```
                                          (SEQ ID NO: 6)
MERHWIFLFLLSVTGGVHSQVQLQQSGAELAKPGTSVQMSCKASGYTFTN
YWMNWIKARPGQGLEWIGATNPNNGYTDYNQRFKDKAILTADKSSNTAYM
HLSSLTSEDSAVYFCASGGHLAYWGQGTVVTVSA
```

SEQ ID NO: 7 is the nucleotide sequence encoding the murine 5C1 light chain variable region with sequence encoding signal peptide (underlined).

```
                                          (SEQ ID NO: 7)
ATGAAGTTGCCTGTTAGGCTGTTGGTGCTGATGTTCTGGATTCCTGCTTC
CAGCAGTGATGTTGTGATGACCCAAATTCCACTCTACCTGTCTGTCAGTC
CTGGAGATCAAGCCTCCATCTCTTGCAGATCTAGTCAGAGCCTTTTCCAT
AGTAAAGGAAACACCTATTTACATTGGTATCTGCAGAAGCCAGGCCAGTC
```

-continued

```
TCCAAAGCTCCTGATCAACAGGGTTTCCAACCGATTTTCTGGGGTCCCAG
ACAGGTTCAGTGGCAGTGGATCAGGGACAGATTTCACACTCAAGATCAGC
GGAGTGGAGGCTGAAGATCTGGGAGTTTATTTCTGTTCTCAAAGTGCACA
TGTTCCGTGGACGTTCGGTGGAGGCACCAAGCTGGAAATCAGA
```

SEQ ID NO: 8 is the murine 5C1 light chain variable region sequence with signal peptide (underlined)

```
                                          (SEQ ID NO: 8)
MKLPVRLLVLMFWIPASSSDVVMTQIPLYLSVSPGDQASISCRSSQSLFH
SKGNTYLHWYLQKPGQSPKLLINRVSNRFSGVPDRFSGSGSGTDFTLKIS
GVEAEDLGVYFCSQSAHVPWTFGGGTKLEIR
```

SEQ ID NO: 9 is the murine 5C1 mature heavy chain variable region with the CDRs underlined. The underlined CDRs are as defined by Kabat except the underlined CDRH1 is a composite of Kabat and Chothia definitions.

```
                                          (SEQ ID NO: 9)
QVQLQQSGAELAKPGTSVQMSCKASGYTFTNYWMNWIKARPGQGLEWIGAT
NPNNGYTDYNQRFKDKAILTADKSSNTAYMHLSSLTSEDSAVYFCASGGHL
AYWGQGTVVTVSA
```

SEQ ID NO: 10 is the sequence of the 5C1 heavy chain CDR1.

(SEQ ID NO: 10)
NYWMN

SEQ ID NO: 11 is the sequence of the 5C1 heavy chain CDR2.

(SEQ ID NO: 11)
ATNPNNGYTDYNQRFKD

SEQ ID NO: 12 is the sequence of the 5C1 heavy chain CDR3.

GGHLAY (SEQ ID NO: 12)

SEQ ID NO: 13 is the human VH Acceptor FR (Acc#AAY42876.1).

```
                                          (SEQ ID NO: 13)
QVQLVQSGAEVKKPGSSVKVSCKASGGTFNNYAINWVRQAPGQGLEWMGG
IIPIFGTTTYAQKFQGRVTITADESTNTAYMELSSLRSEDTAVYYCAREG
NLNWLDPWGQGTLVTVSS
```

SEQ ID NO: 14 is the sequence of humanized 5C1H1.

```
                                          (SEQ ID NO: 14)
QVQLVQSGAELKKPGSSVKVSCKASGYTFTNYWMNWVRQAPGQGLEWIGA
TNPNNGYTDYNQRFKDRATLTADKSTNTAYMELSSLRSEDTAVYYCARGG
HLAYWGQGTLVTVSS
```

SEQ ID NO: 15 is the sequence of humanized 5C1H2.

(SEQ ID NO: 15)
QVQLVQSGAELKKPGSSVKVSCKASGYTFTNYWMNWVRQAPGQGLEWIGA
TNPNNGYTDYNQRFKDRVTITADKSTNTAYMELSSLRSEDTAVYYCARGG
HLAYWGQGTLVTVSS

SEQ ID NO: 16 is the sequence of humanized 5C1H3.

(SEQ ID NO: 16)
QVQLVQSGAELKKPGSSVKVSCKASGYTFTNYWMNWVRQAPGQGLEWIGA
TNPNNGYTDYNQRFKDRATLTADKSTNTAYMELSSLRSEDTAVYFCASGG
HLAYWGQGTLVTVSS

SEQ ID NO: 17 is the sequence of humanized 5C1H4.

(SEQ ID NO: 17)
QVQLVQSGAELKKPGSSVKVSCKASGYTFTNYWMNWVRQAPGQGLEWIGA
TNPNNGYTDYNQRFKDRATLTADKSTNTAYMELSSLRSEDTAVYYCASGG
HLAYWGQGTLVTVSS

SEQ ID NO: 18 is the sequence of humanized 5C1H5.

(SEQ ID NO: 18)
QVQLVQSGAELKKPGSSVKVSCKASGYTFTNYWMNWVRQAPGQGLEWIGA
TNPNNGYTDYNQRFKDRVTITADKSTNTAYMELSSLRSEDTAVYYCASGG
HLAYWGQGTLVTVSS

SEQ ID NO: 19 is the nucleic acid sequence encoding humanized 5C1H1 with sequence encoding signal peptide (underlined).

(SEQ ID NO: 19)
ATGGAGTTCGGCCTGTCCTGGCTGTTCCTGGTGGCCATCCTGAAGGGCGT
GCAGTGCCAGGTGCAGCTGGTGCAGTCCGGCGCCGAGCTGAAGAAGCCCG
GCTCCTCCGTGAAGGTGTCCTGCAAGGCCTCCGGCTACACCTTCACCAAC
TACIGGATGAACTGGGTGCGCCAGGCCCCCGGCCAGGGCCTGGAGTGGAT
CGGCGCCACCAACCCCAACAACGGCTACACCGACTACAACCAGCGCTTCA
AGGACCGCGCCACCCTGACCGCCGACAAGTCCACCAACACCGCCTACATG
GAGCTGTCCTCCCTGCGCTCCGAGGACACCGCCGTGTACTACTGCGCCCG
CGGCGGCCACCTGGCCTACTGGGGCCAGGGCACCCTGGTGACCGTGTCCT
CC

SEQ ID NO: 20 is the nucleic acid sequence encoding humanized 5C1H2 with sequence encoding signal peptide (underlined).

(SEQ ID NO: 20)
ATGGAGTTCGGCCTGTCCTGGCTGTTCCTGGTGGCCATCCTGAAGGGCGT
GCAGTGCCAGGTGCAGCTGGTGCAGTCCGGCGCCGAGCTGAAGAAGCCCG
GCTCCTCCGTGAAGGTGTCCTGCAAGGCCTCCGGCTACACCTTCACCAAC
TACTGGATGAACTGGGTGCGCCAGGCCCCCGGCCAGGGCCTGGAGTGGAT

-continued
CGGCGCCACCAACCCCAACAACGGCTACACCGACTACAACCAGCGCTTCA
AGGACCGCGTGACCATCACCGCCGACAAGTCCACCAACACCGCCTACATG
GAGCTGTCCTCCCTGCGCTCCGAGGACACCGCCGTGTACTACTGCGCCCG
CGGCGGCCACCTGGCCTACTGGGGCCAGGGCACCCTGGTGACCGTGTCCT
CC SEQ ID NO: 21 is the nucleic acid sequence encoding humanized 5C1H3 with sequence encoding signal peptide (underlined).

(SEQ ID NO: 21)
ATGGAGTTCGGCCTGTCCTGGCTGTTCCTGGTGGCCATCCTGAAGGGCGT
GCAGTGCCAGGTGCAGCTGGTGCAGTCCGGCGCCGAGCTGAAGAAGCCCG
GCTCCTCCGTGAAGGTGTCCTGCAAGGCCTCCGGCTACACCTTCACCAAC
TACTGGATGAACTGGGTGCGCCAGGCCCCCGGCCAGGGCCTGGAGTGGAT
CGGCGCCACCAACCCCAACAACGGCTACACCGACTACAACCAGCGCTTCA
AGGACCGCGCCACCCTGACCGCCGACAAGTCCACCAACACCGCCTACATG
GAGCTGTCCTCCCTGCGCTCCGAGGACACCGCCGTGTACTTCTGCGCCTC
CGGCGGCCACCTGGCCTACTGGGGCCAGGGCACCCTGGTGACCGTGTCCT
CC

SEQ ID NO: 22 is the nucleic acid sequence encoding humanized 5C1H4 with sequence encoding signal peptide (underlined).

(SEQ ID NO: 22)
ATGGAGTTCGGCCTGTCCTGGCTGTTCCTGGTGGCCATCCTGAAGGGCGT
GCAGTGCCAGGTGCAGCTGGTGCAGTCCGGCGCCGAGCTGAAGAAGCCCG
GCTCCTCCGTGAAGGTGTCCTGCAAGGCCTCCGGCTACACCTTCACCAAC
TACTGGATGAACTGGGTGCGCCAGGCCCCCGGCCAGGGCCTGGAGTGGAT
CGGCGCCACCAACCCCAACAACGGCTACACCGACTACAACCAGCGCTTCA
AGGACCGCGCCACCCTGACCGCCGACAAGTCCACCAACACCGCCTACATG
GAGCTGTCCTCCCTGCGCTCCGAGGACACCGCCGTGTACTACTGCGCCTC
CGGCGGCCACCTGGCCTACTGGGGCCAGGGCACCCTGGTGACCGTGTCCT
CC

SEQ ID NO: 23 is the nucleic acid sequence encoding humanized 5C1H5 with sequence encoding signal peptide (underlined).

(SEQ ID NO: 23)
ATGGAGTTCGGCCTGTCCTGGCTGTTCCTGGTGGCCATCCTGAAGGGCGT
GCAGTGCCAGGTGCAGCTGGTGCAGTCCGGCGCCGAGCTGAAGAAGCCCG
GCTCCTCCGTGAAGGTGTCCTGCAAGGCCTCCGGCTACACCTTCACCAAC
TACTGGATGAACTGGGTGCGCCAGGCCCCCGGCCAGGGCCTGGAGTGGAT
CGGCGCCACCAACCCCAACAACGGCTACACCGACTACAACCAGCGCTTCA
AGGACCGCGTGACCATCACCGCCGACAAGTCCACCAACACCGCCTACATG
GAGCTGTCCTCCCTGCGCTCCGAGGACACCGCCGTGTACTACTGCGCCAG

-continued

CGGCGGCCACCTGGCCTACTGGGGCCAGGGCACCCTGGTGACCGTGTCCT

CC

SEQ ID NO: 24 is the murine 5C1 mature light chain variable region sequence with the CDRs underlined. The underlined CDRs are as defined by Kabat.

(SEQ ID NO: 24)
DVVMTQIPLYLSVSPGDQASISCRSSQSLFHSKGNTYLHWYLQKPGQSPK

LLINRVSNRFSGVPDRFSGSGSGTDFTLKISGVEAEDLGVYFCSQSAHVP

WTFGGGTKLEIR

SEQ ID NO: 25 is the sequence of the 5C1 light chain CDR1.

RSSQSLFHSKGNTYLH (SEQ ID NO: 25)

SEQ ID NO: 26 is the sequence of the 5C1 light chain CDR2.

RVSNRFS (SEQ ID NO: 26)

SEQ ID NO: 27 is the sequence of the 5C1 light chain CDR3.

(SEQ ID NO: 27)
SQSAHVPWT

SEQ ID NO: 28 is the human VL Acceptor FR (Acc#CAB51293.1).

(SEQ ID NO: 28)
DIVMTQSPLSLPVTPGEPASISCRSSQSLLHSNGYNYLDWYLQKPGQSPQ

LLIYLGSNRASGVPDRFSGSGSGTDFTLKISRVEAEDVGVYYCMQALQTP

PTFGGGTKVEIK

SEQ ID NO: 29 is the sequence of humanized 5C1L1.

(SEQ ID NO: 29)
DVVMTQSPLSLSVSPGEPASISCRSSQSLFHSKGNTYLHWYLQKPGQSPK

LLINRVSNRFSGVPDRFSGSGSGTDFTLKISRVEAEDVGVYFCSQSAHVP

WTFGGGTKVEIK

SEQ ID NO: 30 is the sequence of humanized 5C1L2.

(SEQ ID NO: 30)
DIVMTQSPLSLSVSPGEPASISCRSSQSLFHSKGNTYLHWYLQKPGQSPK

LLIYRVSNRFSGVPDRFSGSGSGTDFTLKISRVEAEDVGVYFCSQSAHVP

WTFGGGTKVEIK

SEQ ID NO: 31 is the sequence of humanized 5C1L3.

(SEQ ID NO: 31)
DVVMTQSPLSLSVSPGEPASISCRSSQSLFHSKGNTYLHWYLQKPGQSPQ

LLINRVSNRFSGVPDRFSGSGSGTDFTLKISRVEAEDVGVYFCSQSAHVP

WTFGGGTKVEIK

SEQ ID NO: 32 is the sequence of humanized 5C1L4.

(SEQ ID NO: 32)
DIVMTQSPLSLSVSPGEPASISCRSSQSLFHSKGNTYLHWYLQKPGQSPQ

LLIYRVSNRFSGVPDRFSGSGSGTDFTLKISRVEAEDVGVYFCSQSAHVP

WTFGGGTKVEIK

SEQ ID NO: 33 is the nucleic acid sequence encoding humanized 5C1L1 with sequence encoding signal peptide (underlined).

(SEQ ID NO: 33)
ATGGACATGCGCGTGCCCGCCCAGCTGCTGGGCCTGCTGATGCTGTGGGT

GTCCGGCTCCTCCGGCGACGTGGTGATGACCCAGTCCCCCCTGTCCCTGT

CCGTGTCCCCCGGCGAGCCCGCCTCCATCTCCTGCCGCTCCTCCCAGTCC

CTGTTCCACTCCAAGGGCAACACCTACCTGCACTGGTACCTGCAGAAGCC

CGGCCAGTCCCCCAAGCTGCTGATCAACCGCGTGTCCAACCGCTTCTCCG

GCGTGCCCGACCGCTTCTCCGGCTCCGGCTCCGGCACCGACTTCACCCTG

AAGATCTCCCGCGTGGAGGCCGAGGACGTGGGCGTGTACTTCTGCTCCCA

GTCCGCCCACGTGCCCTGGACCTTCGGCGGCGGCACCAAGGTGGAGATCA

AG

SEQ ID NO: 34 is the nucleic acid sequence encoding humanized 5C1L2 with sequence encoding signal peptide (underlined).

(SEQ ID NO: 34)
ATGGACATGCGCGTGCCCGCCCAGCTGCTGGGCCTGCTGATGCTGTGGGT

GTCCGGCTCCTCCGGCGACATCGTGATGACCCAGTCCCCCCTGTCCCTGT

CCGTGTCCCCCGGCGAGCCCGCCTCCATCTCCTGCCGCTCCTCCCAGTCC

CTGTTCCACTCCAAGGGCAACACCTACCTGCACTGGTACCTGCAGAAGCC

CGGCCAGTCCCCCAAGCTGCTGATCTACCGCGTGTCCAACCGCTTCTCCG

GCGTGCCCGACCGCTTCTCCGGCTCCGGCTCCGGCACCGACTTCACCCTG

AAGATCTCCCGCGTGGAGGCCGAGGACGTGGGCGTGTACTACTGCTCCCA

GTCCGCCCACGTGCCCTGGACCTTCGGCGGCGGCACCAAGGTGGAGATCA

AG

SEQ ID NO: 35 is the nucleic acid sequence encoding humanized 5C1L3 with sequence encoding signal peptide (underlined).

(SEQ ID NO: 35)
ATGGACATGCGCGTGCCCGCCCAGCTGCTGGGCCTGCTGATGCTGTGGGT

GTCCGGCTCCTCCGGCGACGTGGTGATGACCCAGTCCCCCCTGTCCCTGT

CCGTGTCCCCCGGCGAGCCCGCCTCCATCTCCTGCCGCTCCTCCCAGTCC

CTGTTCCACTCCAAGGGCAACACCTACCTGCACTGGTACCTGCAGAAGCC

CGGCCAGTCCCCCCAGCTGCTGATCAACCGCGTGTCCAACCGCTTCTCCG

GCGTGCCCGACCGCTTCTCCGGCTCCGGCTCCGGCACCGACTTCACCCTG

AAGATCTCCCGCGTGGAGGCCGAGGACGTGGGCGTGTACTTCTGCTCCCA

-continued

GTCCGCCCACGTGCCCTGGACCTTCGGCGGCGGCACCAAGGTGGAGATCA

AG

SEQ ID NO: 36 is the nucleic acid sequence encoding humanized 5C1L4 with sequence encoding signal peptide (underlined).

(SEQ ID NO: 36)
<u>ATGGACATGCGCGTGCCCGCCCAGCTGCTGGGCCTGCTGATGCTGTGGGT</u>

<u>GTCCGGCTCCTCCGGC</u>GACATCGTGATGACCCAGTCCCCCCTGTCCCTGT

CCGTGTCCCCCGGCGAGCCCGCCTCCATCTCCTGCCGCTCCTCCCAGTCC

CTGTTCCACTCCAAGGGCAACACCTACCTGCACTGGTACCTGCAGAAGCC

CGGCCAGTCCCCCCAGCTGCTGATCTACCGCGTGTCCAACCGCTTCTCCG

GCGTGCCCGACCGCTTCTCCGGCTCCGGCTCCGGCACCGACTTCACCCTG

AAGATCTCCCGCGTGGAGGCCGAGGACGTGGGCGTGTACTACTGCTCCCA

GTCCGCCCACGTGCCCTGGACCTTCGGCGGCGGCACCAAGGTGGAGATCA

AG

SEQ ID NO: 37 is the nucleic acid sequence encoding an exemplary human IgG1 constant region.

(SEQ ID NO: 37)
GCCTCCACCAAGGGCCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCACATCTGCAA

CGTGAATCACAAGCCCAGCAACACCAAGGTGGACAAGAGAGTTGAGCCCA

AATCTTGTGACAAAACTCACACATGCCCACCGTGCCCAGCACCTGAACTC

CTGGGGGGACCGTCAGTCTTCCTCTTCCCCCCAAAACCCAAGGACACCCT

CATGATCTCCCGGACCCCTGAGGTCACATGCGTGGTGGTGGACGTGAGCC

ACGAAGACCCTGAGGTCAAGTTCAACTGGTACGTGGACGGCGTGGAGGTG

CATAATGTCAAGACAAAGCCGCGGGAGGAGCAGTACAACAGCACGTACCG

TGTGGTCAGCGTCCTCACCGTCCTGCACCAGGACTGGCTGAATGGCAAGG

AGTACAAGTGCAAGGTCTCCAACAAAGCCCTCCCAGCCCCCATCGAGAAA

ACCATCTCCAAAGCCAAAGGGCAGCCCCGAGAACCACAGGTGTACACGCT

GCCCCCATCCCGGGAGGAGATGACCAAGAACCAGGTCAGCCTGACCTGCC

TGGTCAAAGGCTTCTATCCCAGCGACATCGCGTGGAGTGGGAGAGCAATG

GGCAGCCGGAGAACAACTACAAGACCACGCCTCCCGTGCTGGACTCCGAC

GGCTCCTTCTTCCTCTATAGCAAGCTCACCGTGGACAAGAGCAGGTGGCA

GCAGGGGAACGTCTTCTCATGCTCCGTGATGCATGAGGCTCTGCACAACC

ACTACACGCAGAAGAGCCTCTCCCTGTCCCCGGGTAAATGA

SEQ ID NO: 38 is the amino acid sequence of an exemplary human IgG1 constant region.

(SEQ ID NO: 38)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNVKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

SEQ ID NO: 39 is the nucleic acid sequence encoding an exemplary human kappa light chain constant region.

(SEQ ID NO: 39)
ACTGTGGCTGCACCATCTGTCTTCATCTTCCCGCCATCTGATGAGCAGTT

GAAATCTGGAACTGCCTCTGTTGTGTGCCTGCTGAATAACTTCTATCCCA

GAGAGGCCAAAGTACAGTGGAAGGTGGATAACGCCCTCCAATCGGGTAAC

TCCCAGGAGAGTGTCACAGAGCAGGACAGCAAGGACAGCACCTACAGCCT

CAGCAGCACCCTGACGCTGAGCAAAGCAGACTACGAGAAACACAAAGTCT

ACGCCTGCGAAGTCACCCATCAGGGCCTGAGCTCGCCCGTCACAAAGAGC

TTCAACAGGGGAGAGTGTTAG

SEQ ID NO: 40 is the amino acid sequence of an exemplary human kappa light chain constant region.

(SEQ ID NO: 40)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

SEQ ID NO: 41 is the amino acid sequence of residues 118-126 of α-synuclein.

(SEQ ID NO: 41)
VDPDNEAYE

DEFINITIONS

The basic antibody structural unit is a tetramer of sub-units. Each tetramer includes two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. When initially expressed, this variable region is typically linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function. A constant region can include any or all of a CH1 region, hinge region, CH2 region, and CH3 region.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except for bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the regions FR1, CDR1, FR2, CDR2, FR3, CDR3 and FR4. The assignment of amino acids to each region is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number (e.g., H83 means position 83 by Kabat numbering in the mature heavy chain variable region; likewise position L36 means position 36 by Kabat numbering in the mature light chain variable region). Kabat numbering is used throughout in referring to positions in the variable region of an antibody unless explicitly stated otherwise.

The term "antibody" includes intact antibodies and binding fragments thereof. Typically, fragments compete with the intact antibody from which they were derived for specific binding to the target. Fragments include separate heavy chains, separate light chains, Fab, Fab', F(ab')2, F(ab)c, Fv, single chain antibodies, and single domain antibodies. Single (variable) domain antibodies include VH regions separated from their VL partners (or vice versa) in conventional antibodies (Ward et al., 1989, Nature 341: 544-546), as well as VH regions (sometimes known as VHH) from species such as Camelidae or cartilaginous fish (e.g., a nurse shark) in which VH regions are not associated with VL regions (see, e.g., WO 9404678). Single domain antibodies in which one chain is separated from its natural partners are sometimes known as Dabs and single domain antibodies from Caemelidae or cartilaginous fish are sometimes known as nanobodies. Constant regions or parts of constant regions may or may not be present in single domain antibodies. For example, natural single variable region antibodies from Camelidae include a VHH variable region, and CH2 and CH3 constant regions. Single domain antibodies, such as nanobodies, can be subject to humanization by analogous approaches to conventional antibodies. Dabs antibodies are usually obtained from antibodies of human origin. Fragments can be produced by recombinant DNA techniques, or by enzymatic or chemical separation of intact immunoglobulins.

The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol. 148:1547-53 (1992)). In some bispecific antibodies, the two different heavy/light chain pairs include a humanized 5C1 heavy chain/light chain pair and a heavy chain/light chain pair specific for a different epitope on alpha synuclein than that bound by 5C1.

In some bispecific antibodies, one heavy chain light chain pair is a humanized 5C1 antibody as further disclosed below and the heavy light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., PNAS 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal. et al. *Sci. Trans. Med.* 3, 84ra43, 2011; Yu et al. *Sci. Trans. Med.* 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

An "antigen" is an entity to which an antibody specifically binds.

The term "epitope" refers to a site on an antigen to which an antibody binds. For protein antigens, an epitope can be formed from contiguous amino acids or noncontiguous amino acids juxtaposed by tertiary folding of one or more proteins. Epitopes formed from contiguous amino acids are typically retained on exposure to denaturing solvents, whereas epitopes formed by tertiary folding are typically lost on treatment with denaturing solvents. An epitope typically includes at least 2, 3, and more usually, at least 5 or 8-10 amino acids in a unique spatial conformation. Methods of determining spatial conformation of epitopes include, for example, X-ray crystallography and 2-dimensional nuclear magnetic resonance. See, e.g., Epitope Mapping Protocols, in Methods in Molecular Biology, Vol. 66, Glenn E. Morris, Ed. (1996). An epitope can include a C-terminal residue or an N-terminal residue. An epitope can also include, but need not include, the free amino group of a polypeptide or the free carboxyl group of a polypeptide. Thus, an epitope can include a C-terminal or an N-terminal residue, but not necessarily include the free carboxyl group or the free amino group, respectively. Antibody binding specificity is sometimes defined by a range of amino acids. If an antibody is said to bind to an epitope within amino acids 118-126 of SEQ ID NO:1, for example, what is meant is that the epitope is within the recited range of amino acids including those defining the outer-limits of the range. It does not necessarily mean that every amino acid within the range constitutes part of the epitope. Thus, for example, an epitope within amino acids 118-126 of SEQ ID NO:1 may consist of amino acids 118-124, 119-125, 120-126, 120-124, or 120-122, among other segments of SEQ ID NO:1.

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues (the epitope being defined by the residues making contact). Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen. See, e.g., Junghans et al. (1990), Cancer Res. 50:1495. A test antibody competes with a reference antibody if an excess of a test antibody (e.g., at least 2×, 5×, 10×, 20× or 100×) inhibits binding of the reference antibody by at least 50%, 75%, 90%, 95%, 98%, or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

Antibodies of the invention typically bind to their designated target with an affinity constant of at least $10^6$, $10^7$, $10^8$, $10^9$, or $10^{10}$ $M^{-1}$. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

When comparing antibody sequences, percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Monoclonal antibodies are typically provided in isolated form. This means that the antibody is typically at least 50% w/w pure of interfering proteins and other contaminants arising from its production or purification, but does not exclude the possibility that the agent is combined with an excess of pharmaceutically-acceptable carrier(s) or other vehicle intended to facilitate its use. Sometimes monoclonal antibodies are at least 60%, 70%, 80%, 90%, 95%, 96%, 97%, 98%, or 99% w/w pure of aggregates or fragments of such monoclonal antibodies or of other proteins and contaminants. Some such monoclonal antibodies may include aggregates or fragments but are at least 99% w/w pure of other proteins and contaminants.

Compositions or methods "comprising" one or more recited elements may include other elements not specifically recited. For example, a composition that comprises antibody may contain the antibody alone or in combination with other ingredients.

Designation of a range of values includes all integers within or defining the range, and all subranges defined by integers within the range.

Unless otherwise apparent from the context, the term "about" encompasses values within the margin of error of measurement (SEM) of a stated value.

Statistical significance means $p \leq 0.05$.

A "patient" includes a human or other mammalian subject that receives either prophylactic or therapeutic treatment.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor.

The term "symptom" refers to a subjective evidence of a disease, such as altered gait, as perceived by the patient. A "sign" refers to objective evidence of a disease as observed by a physician.

"Cognitive function" refers to mental processes such as any or all of attention, memory, producing and understanding language, solving problems, and taking an interest in one's surroundings and self-care.

"Enhanced cognitive function" or "improved cognitive function" refers to improvement relative to a baseline, for example, diagnosis or initiation of treatment. "Decline of cognitive function" refers to a decrease in function relative to such a base line.

In animal model systems such as rat or mouse, cognitive function may be measured methods including using a maze in which subjects use spatial information (e.g., Morris water maze, Barnes circular maze, elevated radial arm maze, T maze and others), fear conditioning, active avoidance, illuminated open-field, dark activity meter, elevated plus-maze, two-compartment exploratory test or forced swimming test.

In humans, cognitive function can be measured by one or more of several standardized tests. Examples of a test or assay for cognitive function were described (Ruoppila and Suutama, Scand. J. Soc. Med. Suppl. 53,44-65, 1997) and include standardized psychometric tests (e. g. Wechsler Memory Scale, the Wechsler Adult Intelligence Scale, Raven's Standard Progressive Matrices, Schaie-Thurstone Adult Mental Abilities Test), neuropsychological tests (e. g. Luria-Nebraska), metacognitive self-evaluations (e. g.

Metamemory Questionnaire), visual-spatial screening tests (e.g. Poppelreuter's Figures, Clock Recognition, Honeycomb Drawing and Cancellation), cognitive screening tests (e. g. Folstein's Mini Mental State Test) and reaction time tests. Other standard tests for cognitive performance include the Alzheimer's Disease Assessment Scale-cognitive subscale (ADAS-cog); the clinical global impression of change scale (CIBIC-plus scale); the Alzheimer's Disease Cooperative Study Activities of Daily Living Scale (ADCS-ADL); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG), Stroop Test, Trail Making, Wechsler Digit Span, and the CogState computerized cognitive test. In addition, cognitive function may be measured using imaging techniques such as Positron Emission Tomography (PET), functional magnetic resonance imaging (fMRI), Single Photon Emission Computed Tomography (SPECT), or any other imaging technique that allows one to measure brain function.

DETAILED DESCRIPTION OF THE INVENTION

I. General

The invention provides monoclonal antibody 5C1 and related antibodies, such as antibodies that bind to the same epitope on α-synuclein (i.e., an epitope 118-126 of α-synuclein). The antibodies of the invention are useful, for example, for treating disorders associated with α-synuclein accumulation, particularly accumulation in Lewy bodies. Such disorders include Lewy Body Diseases, such as Parkinson's disease, Diffuse Lewy Body Disease (DLBD), Lewy body variant of Alzheimer's disease (LBV), Combined Alzheimer's and Parkinson disease, pure autonomic failure and multiple system atrophy (MSA). The antibodies are also useful for diagnoses of a Lewy Body Diseases.

II. Target Molecules

Natural human wildtype α-synuclein is a peptide of 140 amino acids having the following amino acid sequence:

```
                                          (SEQ ID NO: 1)
MDVFMKGLSKAKEGVVAAAEKTKQGVAEAAGKTKEGVLYVGSKTKEGVV

HGVATVAEKTKEQVTNVGGAVVTGVTAVAQKTVEGAGSIAAATGFVKKD

QLGKNEEGAPQEGILEDMPVDPDNEAYEMPSEEGYQDYEPEA
```

(Uéda et al., Proc. Natl. Acad. Sci. USA, 90:11282-6, 1993; GenBank accession number: P37840). The protein has three recognized domains, a KTKE repeat domain covering amino acids 1-61, a NAC (Non-amyloid component) domain running from about amino acids 60-95, and a C-terminal acidic domain running from about amino acid 98 to 140. Jensen et al. (1995) reported that NAC has the amino acid sequence:

```
                                          (SEQ ID NO: 2)
EQVTNVGGAVVTGVTAVAQKTVEGAGSIAAATGFV
```

(Jensen et al., Biochem. J. 310.1: 91-94; GenBank accession number S56746). However, Ueda et al. (1993) reported that NAC has the amino acid sequence:

```
                                          (SEQ ID NO: 3)
KEQVTNVGGAVVTGVTAVAQKTVEGAGS
```

(Uéda et al., Proc. Natl. Acad. Sci. USA, 90:11282-6).

Unless otherwise apparent from the context, reference to α-synuclein or its fragments includes the natural human wildtype amino acid sequences indicated above, and human allelic variants thereof, particularly those associated with Lewy body disease (e.g., E46K, A30P and A53T, with the first letter indicates the amino acid in SEQ ID NO:1, the number is the codon position in SEQ ID NO:1, and the second letter is the amino acid in the allelic variant). Such variants can optionally be present individually or in any combination. The induced mutations E83Q, A90V, A76T, which enhance alpha synuclein aggregation, can also be present individually or in combination with each other and/or human allelic variants E46K, A30P and A53T.

III. Lewy Body Diseases

Lewy Body Diseases (LBD) are characterized by degeneration of the dopaminergic system, motor alterations, cognitive impairment, and formation of Lewy bodies (LBs) (McKeith et al., Neurology (1996) 47:1113-24). Lewy Bodies are spherical protein deposits found in nerve cells. Their presence in the brain disrupts the brain's normal function interrupting the action of chemical messengers including acetylcholine and dopamine. Lewy Body diseases include Parkinson's disease (including idiopathic Parkinson's disease), Diffuse Lewy Body Disease (DLBD) also known as Dementia with Lewy Bodies (DLB), Lewy body variant of Alzheimer's disease (LBV), Combined Alzheimer's and Parkinson disease and as multiple system atrophy (MSA; e.g., Olivopontocerebellar Atrophy, Striatonigral Degeneration and Shy-Drager Syndrome). DLBD shares symptoms of both Alzheimer's and Parkinson's disease. DLBD differs from Parkinson's disease mainly in the location of Lewy Bodies. In DLBD, Lewy Bodies form mainly in the cortex. In Parkinson's disease, they form mainly in the substantia nigra. Other Lewy Body diseases include Pure Autonomic Failure, Lewy body dysphagia, Incidental LBD, and Inherited LBD (e.g., mutations of the α-synuclein gene, PARK3 and PARK4).

IV. Antibodies

A. Binding Specificity and Functional Properties

5C1 is an exemplary antibody of the invention, whose heavy and light chain mature variable regions are designated SEQ ID NO: 9 and SEQ ID NO: 24, respectively. The invention also provides antibodies competing with 5C1 for binding to α-synuclein, or which bind to the same or overlapping epitope as 5C1, and have similar functional properties, such as reducing neuronal aggregates of α-synuclein, improving cognitive function, and/or preserving synaptic density and/or dentritic density.

Other antibodies having such binding specificity can be produced by immunizing mice with α-synuclein or a fragment thereof (e.g., a fragment including amino acid residues 118-126, or a portion thereof), and screening the resulting antibodies for binding to α-synuclein, optionally in competition with 5C1. Use of a fragment is preferred for generating an antibody having the same epitope as 5C1. Antibodies can also be screened for their effect in: (1) α-synuclein transgenic rodent models subjected to behavioral assays, such as the Morris Water Maze (MWM) test or horizontal beam test, and/or immunological assays for the detection of α-synuclein, α-synuclein aggregation, synaptophysin, MAP2, and/or PSD95 in brain tissue; (2) rodent or other non-human animal models for a disease characterized by α-synuclein accumulation, using behavioral assays such as the Morris Water Maze (MWM) test or horizontal beam test and/or immunological assays for the detection of α-synuclein, α-synuclein aggregation, synaptophysin, MAP2, and/or PSD95 in brain tissue; and/or (3) humans with a condition associated with α-synuclein accumulation, using appropriate behavioral assays. Alternatively, or in addition to any of the foregoing approaches, antibodies can be screened against mutagenized forms of α-synuclein to identify an antibody showing the same or similar binding profile as 5C1 to a collection of mutational changes. The mutations can be systematic substitution with alanine (or serine if an alanine is present already) one residue at a time, or more broadly spaced intervals, throughout α-synuclein or through a section thereof in which the epitope is known to reside (e.g., residues 118-126).

Figure 6:
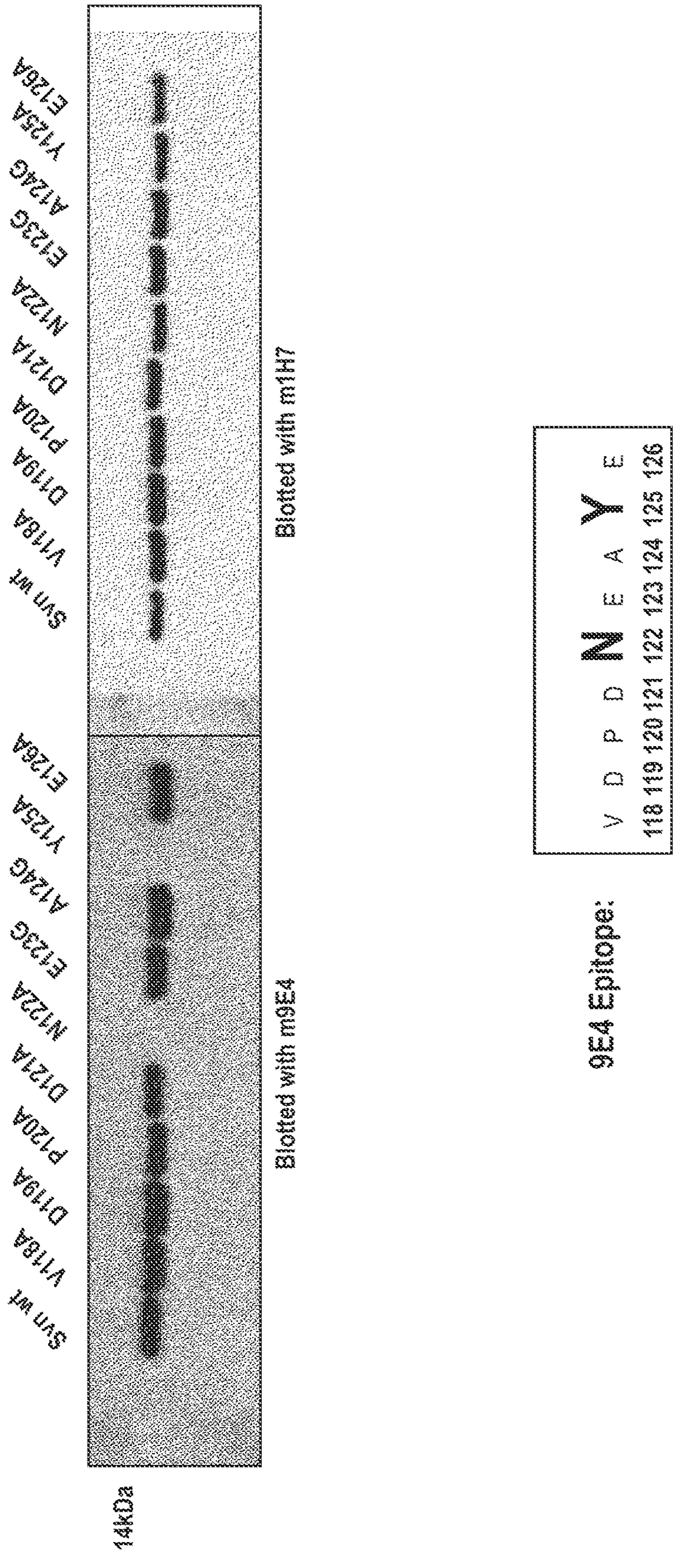
FIG. 6 shows the results of an alanine scanning mutagenesis experiment used to determine the epitope of α-synuclein bound by the 9E4 antibody. The upper portion of the figure shows Western blots of full length α-synuclein (wild-type or individual point mutations of residues 118-126, as indicated) stained with 9E4 antibody (left panel) or control antibody 1H7 (right panel). The lower portion of the figure (SEQ ID NO: 41) shows the epitope of α-synuclein bound by the 9E4 antibody.
Figure 7:
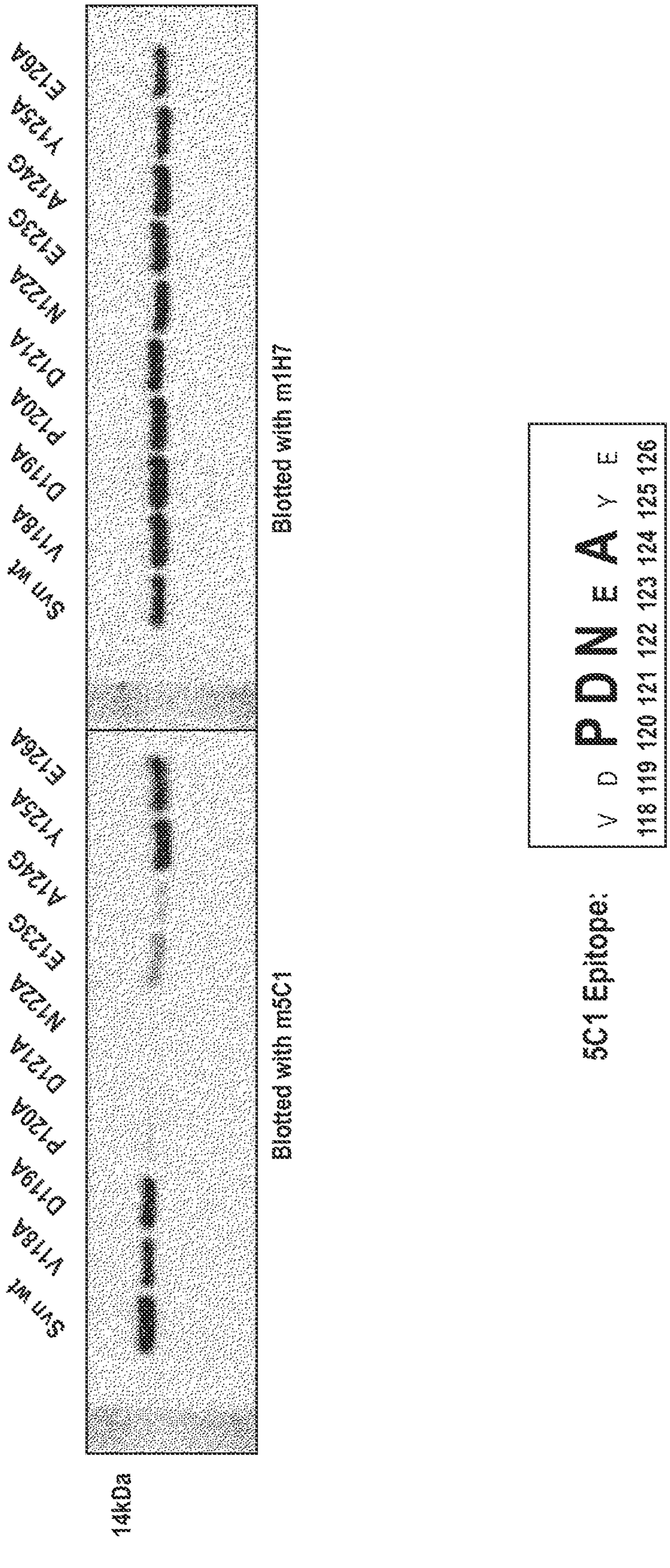
FIG. 7 shows the results of an alanine scanning mutagenesis experiment used to determine the epitope of α-synuclein bound by the 5C1 antibody. The upper portion of the figure shows Western blots of full length α-synuclein (wild-type or individual point mutations in residues 118-126, as indicated) stained with 5C1 antibody (left panel) or control antibody 1H7 (right panel). The lower portion of the figure (SEQ ID NO: 41) shows the epitope of α-synuclein bound by the 5C1 antibody.
Figure 8:
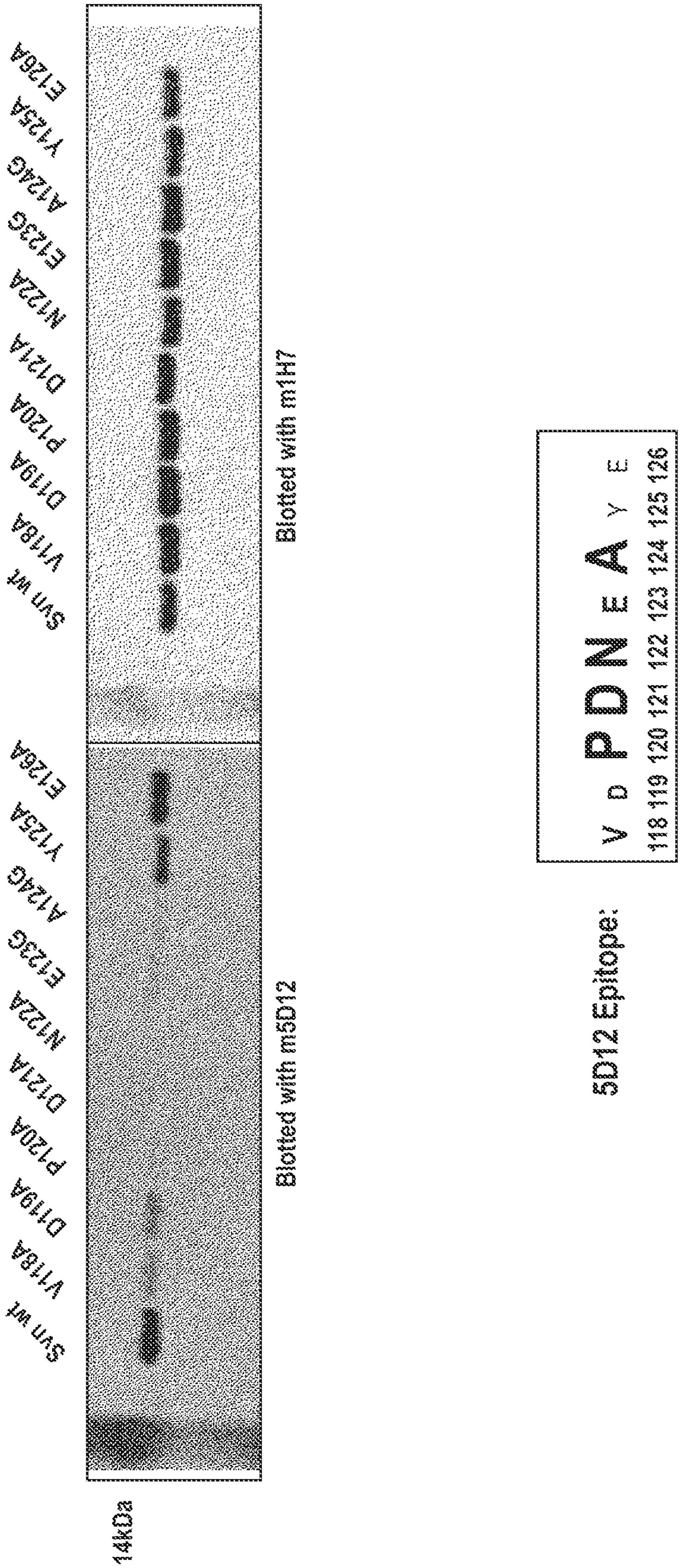
FIG. 8 shows the results of an alanine scanning mutagenesis experiment used to determine the epitope of α-synuclein bound by the 5D12 antibody. The upper portion of the figure shows Western blots of full length α-synuclein (wild-type or individual point mutations in residues 118-126, as indicated) stained with 5D12 antibody (left panel) or control antibody 1H7 (right panel). The lower portion of the figure (SEQ ID NO: 41) shows the epitope of α-synuclein bound by the 5D12 antibody.

FIGS. 6-8 and Example 6 characterize the epitope of 5C1 in comparison with two other antibodies binding within residues 118-126, namely 9E4 and 5D12. Alanine mutagenesis tests the effect of mutating individual amino acids, one at a time, in the 118-126 of alpha synuclein. The profile of relative changes of binding affinity (in other words, contribution to binding) caused by mutation of different amino acids within residues 118-126 characterizes the epitope. For 5C1, mutagenesis of any of residues 120-122 has the greatest reduction of binding. Mutagenesis of residue 123 or 124 results in a significant reduction of binding, but not as much as at any of positions 120-122. Mutagenesis of residue 118, 119, 125 or residue 126 results in still less loss of binding affinity, essentially unchanged. For simplicity, the effects of mutagenesis can be approximately subdivided into three categories: essentially complete reduction of binding for residues 120-122 (indistinguishable from negative control), essentially no reduction of binding for residues 118, 119, 125 and 126 (indistinguishable from positive control) and intermediate reduction of binding affinity for residues 123 and 124. The epitope of 5C1 can thus be approximately characterized as a linear epitope consisting of or consisting essentially of residues 120-124 of SEQ ID NO:1, with residues 120-122 making the greatest contribution to binding. Antibodies having the 5C1 epitope as characterized by any of the descriptions in this paragraph are provided. Some antibodies are characterized by an epitope consisting essentially of residues 120-122 and excluding residues 119-120 meaning that residues 120-122 each contribute more to binding than any other residue and residues 119 and 120 make no detectable contribution to binding (e.g., by the alanine scanning method of the example). Residues 123 and 124 may or may not make a minor contribution to binding in such antibodies.

For 5D12, the epitope is characterized by alanine mutagenesis as follows. Mutagenesis of any of residues 120-122 has the greatest reduction of binding. Mutagenesis of residue 118, 199, 123 or 124 results in significant reduction of binding, but not as much as at any of positions 120-122. Mutagenesis of residue 125 or residue 126 results in still less loss of binding affinity, essentially unchanged. For simplicity, the effects of mutagenesis can be approximately subdivided into three categories: essentially complete reduction of binding for mutation of residues 120-122 (indistinguishable from negative control), essentially no reduction of binding for residues 125 and 126 (indistinguishable from positive control) and intermediate reduction of binding affinity for residues 118, 119, 123 and 124. The epitope of 5D12 can thus be approximately characterized as a linear epitope consisting of or consisting essentially of residues 118-124 of SEQ ID NO:1, with residues 120-122 making the greatest contribution to binding. Other antibodies having the epitope of 5D12 as characterized by any of the descriptions in this paragraph or Example 6 are also provided.

Likewise, the 9E4 epitope can be characterized by mutation of residues 122 and 125 each showing greater reduction of binding than any of residues 118-121, 123, 124 or 126. For simplicity the effects of mutagenesis can be approximately divided into two categories: essentially complete reduction of binding for residues 122 and 125 and essentially no reduction in binding for residues 118-121, 123, 124 and 126. The 9E4 epitope can thus be approximately characterized as a conformational epitope in which residues 122 and 125 provide the contact points (or greatest contribution to binding) with 9E4. Other antibodies having the 9E4 epitope as characterized by any of the descriptions in this paragraph or Example 6 are provided. Optionally, the antibody is not 9E4 or other antibody having the same CDRs as 9E4 nor an antibody having at least five Kabat CDRs with at least 85% sequence identity to the corresponding CDRs of 9E4.

Antibodies having the binding specificity of a selected murine antibody (e.g., 5C1) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for α-synuclein (e.g., at least $10^8$ $M^{-1}$, and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for sa-synuclein are selected. The resulting antibodies usually have the same or similar epitope specificity as the murine starting material.

Other antibodies can be obtained by mutagenesis of cDNA encoding the heavy and light chains of an exemplary antibody, such as 5C1. Accordingly, monoclonal antibodies that are at least 70%, 80%, 90%, 95%, 96%, 97%, 98% or 99% identical to 5C1 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention.

The invention also includes monoclonal antibodies having some or all (e.g., 3, 4, 5, and preferably 6) CDRs entirely or substantially from 5C1. Such antibodies can include a heavy chain variable region that has at least two, and usually all three, CDRs entirely or substantially from the heavy chain variable region of 5C1 and/or a light chain variable region having at least two, and usually all three, CDRs entirely or substantially from the light chain variable region of 5C1. Preferred antibodies include both heavy and light chains. A CDR is substantially from a corresponding 5C1

CDR when it contains no more than 4, 3, 2 or 1 substitutions, insertions or deletions, except that CDRH2 (when defined by Kabat) can have no more than 6, 5, 4, 3, 2, or 1 substitutions, insertion or deletions. Such antibodies preferably have at least 70%, 80%, 90%, 95%, 96%, 97%, 98% or 99% identity to 5C1 in the amino acid sequence of the mature heavy and/or light chain variable regions and maintain its functional properties, and/or differ from 5C1 by a small number of functionally inconsequential amino acid substitutions (e.g., conservative substitutions), deletions, or insertions.

Preferred antibodies show similar functional activity to 5C1, e.g., reducing neuritic and/or axonal α-synuclein aggregates, reducing neuritic dystrophy, improving cognitive function, reversing, treating or inhibiting cognitive decline, and/or preserving or increasing synaptic density and/or dentritic density.

B. Chimeric and Veneered Antibodies

The invention further provides chimeric and veneered forms of non-human antibodies, particularly 5C1.

A chimeric antibody is an antibody in which the mature variable regions of light and heavy chains of a non-human antibody (e.g., a mouse) are combined with human light and heavy chain constant regions. Typically, the light and heavy chain constant regions are of human origin, but the constant regions can originate from a different non-human species as needed (e.g., to facilitate testing of the non-human antibody in an appropriate animal model). Such antibodies substantially or entirely retain the binding specificity of the mouse antibody, and can be about two-thirds human sequence contributed by the human constant regions.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

C. Humanized Antibodies

Humanized 5C1 antibodies specifically bind to human α-synuclein. The affinity of some humanized antibodies (i.e., Ka) is can be, for example, within a factor of five or two of that of the murine 5C1 antibody. Some humanized antibodies have an affinity that is the same, within experimental error, as murine 5C1. Some humanized antibodies have an affinity greater than that of murine 5C1. Preferred humanized antibodies bind to the same epitope and/or compete with murine 5C1 for binding to human α-synuclein.

A humanized antibody is a genetically engineered antibody in which the CDRs from a non-human "donor" antibody (e.g., murine 5C1) are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized 5C1 antibody is an antibody having some or all CDRs entirely or substantially from murine 5C1 and variable region framework sequences and constant regions, if present, entirely or substantially from human antibody sequences. Similarly a humanized heavy chain has at least two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. Preferably at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region, respectively, when at least 85%, 90%, 95%, 96%, 97%, 98%, 99%, or 100% of corresponding residues defined by Kabat are identical.

Although humanized antibodies often incorporate all six CDRs (preferably as defined by Kabat) from a mouse antibody, they can also be made with less than all CDRs (at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

In some antibodies only part of the CDRs, namely the subset of CDR residues required for binding, termed the specificity determining residues (SDRs) (Kashmiri et al., Methods (2005) 36 (1):25-34), are needed to retain binding in a humanized antibody. CDR residues not contacting antigen and not in the SDRs can be identified based on previous studies (for example one or more or all of residues H60-H65 in CDR H2 are sometimes not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863, 2004. In such humanized antibodies, at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65%-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g. is within about 6 Å of a CDR region), (e.g., identified by modeling the light or heavy chain on the solved structure of a homologous known immunoglobulin chain); and (4) a residue participating in the VL-VH interface.

Framework residues from classes (1)-(3) as defined by Queen, U.S. Pat. No. 5,530,101 are sometimes alternately referred to as canonical and vernier residues. Framework residues that help define the conformation of a CDR loop are sometimes referred to as canonical residues (Chothia and Lesk, J. Mol. Biol. 196, 901-917 (1987), Thornton & Martin J. Mol. Biol., 263, 800-815, 1996). Framework residues that support antigen-binding loop conformations and play a role in fine-tuning the fit of an antibody to antigen are sometimes referred to as vernier residues (Foote & Winter, 1992, *J Mol Bio.* 224, 487-499).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

The invention provides humanized forms of the mouse 5C1 antibody. The mouse antibody comprises mature heavy and light chain variable regions having amino acid sequences comprising SEQ ID NO: 9 and SEQ ID NO: 24, respectively. The invention provides five exemplified humanized mature heavy chain variable regions: H1, SEQ ID NO: 14; H2, SEQ ID NO: 15; H3, SEQ ID NO: 16; H4, SEQ ID NO: 17; and H5, SEQ ID NO: 18. The invention further provides four exemplified humanized mature light chain variable regions: L1, SEQ ID NO: 29; L2, SEQ ID NO: 30; L3, SEQ ID NO: 31; and L4, SEQ ID NO: 32. Antibodies include any permutations of these mature heavy and light chain variable regions are provided, i.e., H1L2, H1L3, H1L4, H2L1, H2L2, H2L3, H2L4, H3L1, H3L2, H3L3, H3L4, H4L1, H4L2, H4L3, H4L4, H5L1, H5L2, H5L3, or H5L4. The H4L3 variant, which includes eight heavy chain backmutations and five light chain backmutations, has an affinity to α-synuclein (as measured on a Biacore instrument) that is within a factor of two of the affinities of the murine and chimeric 5C1 antibodies. See Table 1, below. As measured by ELISA, the H4L3 variant has an affinity for α-synuclein that is substantially the same as a chimeric 5C1 antibody (within experimental error) and superior to the murine 5C1 antibody. See FIG. 5. In addition, the H5L3 variant, which includes six heavy chain backmutations and five light chain backmutations, provides an affinity to human α-synuclein (as measured on a Biacore instrument) that is within a factor of four the affinities of the murine and chimeric 5C1 antibodies. See Table 1, below. The H3L4 variant, which includes nine heavy chain backmutations and two light chain backmutations, also provides an affinity to human α-synuclein (as measured by ELISA) that is substantially the same a chimeric 5C1 antibody, within experimental error, and the H3L3 and H3L1 variants, which each include nine heavy chain backmutations and five and six light chain backmutations, respectively, provide affinities to α-synuclein that are superior to the murine 5C1 antibody (as measured by ELISA).

The invention provides variants of the H4L3 humanized 5C1 antibody in which the humanized mature heavy chain variable region shows at least 90%, 95%, 96%, 97%, 98%, or 99% identity to H4 (SEQ ID NO: 17) and the humanized mature light chain variable region shows at least 90%, 95%, 96%, 97%, 98%, or 99% sequence identity to L3 (SEQ ID NO: 31). In some such antibodies, at least one, two, three, four, five, six, seven, eight, nine, ten, eleven, twelve, or all thirteen of the backmutations in H4L3 are retained. The invention also provides variants of the H5L3 humanized 5C1 antibody in which the humanized mature heavy chain variable region shows at least 90%, 95%, 96%, 97%, 98%, or 99% identity to H5 (SEQ ID NO: 18) and the humanized mature light chain variable region shows at least 90%, 95%, 96%, 97%, 98%, or 99% sequence identity to L3 (SEQ ID NO: 31). In some such antibodies, at least one, two, three, four, five, six, seven, eight, nine, ten, or all eleven of the backmutations in H5L3 are retained. The invention also provides variants of the H3L4 humanized 5C1 antibody in which the humanized mature heavy chain variable region shows at least 90%, 95%, 96%, 97%, 98%, or 99% identity to H3 (SEQ ID NO: 16) and the humanized mature light chain variable region shows at least 90%, 95%, 96%, 97%, 98%, or 99% sequence identity to L4 (SEQ ID NO: 32). In some such antibodies, at least one, two, three, four, five, six, seven, eight, nine, ten, or all eleven of the backmutations in H3L4 are retained. In some antibodies, at least one of positions H11, H27, H30, H48, and H73 in the Vh region is occupied by L, Y, T, I, and K, respectively. In some antibodies, positions H11, H27, H30, H48, and H73 in the Vh region are occupied by L, Y, T, I, and K, respectively. In some antibodies, at least one of positions H67, H69, H91, and H94 in the Vh region is occupied by A, L, F, and S, respectively. In some antibodies, positions H67, H69, and H94 in the Vh region are occupied by A, L, and S, respectively, such as in version H4. In some antibodies, position H94 is occupied by S, such as in version H5. In some antibodies, positions H67, H69, H91, and H94 in the Vh region are occupied by A, L, F, and S, respectively, such as in version H3. In some antibodies, at least one of positions L12 and L14 in the Vk region is occupied by S. In some antibodies, positions L12 and L14 in the Vk region are both occupied by S, such as in versions L3 and L4. In some antibodies, at least one of positions L2, L45, L49, and L87 in the Vk region is occupied by V, K, N, and F, respectively. In some antibodies, positions L2, L49, and L87 in the Vk region are occupied by V, N, and F, respectively, such as in version L3. In some antibodies, positions L2, L45, L49, and L87 in the Vk region are occupied by V, K, N, and F, respectively, such as in version L1. The CDR regions of such humanized antibodies can be identical or substantially identical to the CDR regions of H4L3 or H5L3, which are the same as those of the mouse donor antibody. The CDR regions can be defined by any conventional definition (e.g., Chothia) but are preferably as defined by Kabat.

One possibility for additional variation in humanized 5C1 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution or even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutation. For example, when using a heavy chain acceptor sequence in which position H11 is already occupied by L, H48 is already occupied by I, and/or H73 is already occupied by K, the corresponding backmutation(s) is not necessary. Similarly, when using a light chain acceptor sequence in which position L12 and/or L14 is occupied by S, the corresponding backmutation(s) is not necessary.

The invention also includes humanized antibodies in which the mature light and heavy chain variable regions shows at least 90%, 95%, 96%, 97%, 98%, or 99% sequence identity to the mature light and heavy chain variable regions of the humanized 5C1 H1L1, H1L2, H1L3, H1L4, H2L1, H2L2, H2L3, H2L4, H3L1, H3L2, H3L3, H4L1, H4L2, H4L4, H5L1, H5L2, or H5L4. The CDR regions of such humanized antibodies can be identical or substantially identical to those of the mouse donor antibody. The CDR regions can be defined by any conventional definition (e.g., Chothia) but are preferably as defined by Kabat.

D. Selection of Constant Region

The heavy and light chain variable regions of chimeric, humanized (including veneered), or human antibodies can be linked to at least a portion of a constant region sufficient to interact with an Fc receptor. The constant region is typically human, but a non-human constant region can be selected as needed.

The choice of constant region depends, in part, on whether antibody-dependent complement and/or cellular mediated cytotoxicity is desired. For example, human isotopes IgG1 and IgG3 have complement-mediated cytotoxicity whereas human isotypes IgG2 and IgG4 have poor or no complement-mediated cytotoxicity. A human IgG1 constant region suitable for inclusion in the antibodies of the invention can have the sequence of SEQ ID NO: 38. Light chain constant regions can be lambda or kappa. A human kappa light chain constant region suitable for inclusion in the antibodies of the invention can have the sequence of SEQ ID NO: 40. Antibodies can be expressed as tetramers containing two light and two heavy chains, as separate heavy chains, as separate light chains, as Fab, Fab', $F(ab')_2$, or Fv fragments, or as single chain antibodies in which heavy and light chain variable regions are linked through a spacer.

Human constant regions show allotypic variation and isoallotypic variation between different individuals. That is, the constant regions can differ in different individuals at one or more polymorphic positions. Isoallotypes differ from allotypes in that sera recognizing an isoallotype binds to a non-polymorphic region of one or more other isotypes. Reference to a human constant region includes a constant region with any natural allotype or any permutation of residues occupying polymorphic positions in natural allotypes or up to 3, 5 or 10 substitutions for reducing or increasing effector function as described below.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduces affinity for Fcγ receptors, particularly FcγRI receptor (see, e.g., U.S. Pat. No. 6,624,821). An alanine substitution at positions 234, 235 and 237 of human IgG1 can be used for reducing effector functions. Optionally, positions 234, 236 and/or 237 in human IgG2 are substituted with alanine and position 235 with glutamine. (See, e.g., U.S. Pat. No. 5,624,821). In some aspects, a mutation at one or more of positions 241, 264, 265, 270, 296, 297, 322, 329, and 331 by EU numbering of human IgG1 is used. In some aspects, a mutation at one or more of 318, 320, and 322 by EU numbering of human IgG1 is used. In some aspects, the isotype is human IgG2 or IgG4.

E. Human Antibodies

Human antibodies against α-synuclein are provided by a variety of techniques described below. Some human antibodies are selected by competitive binding experiments, or otherwise, to have the same or overlapping epitope specificity as 5C1. Human antibodies can also be screened for a particular epitope specificity by using only a fragment of α-synuclein (e.g., amino acid residues 118-126) as the immunogen, and/or by screening antibodies against a collection of deletion mutants of α-synuclein. One technique for producing human antibodies is trioma methodology (Oestberg et al., Hybridoma 2:361-367 (1983); Oestberg, U.S. Pat. No. 4,634,664; and Engleman et al., U.S. Pat. No. 4,634,666). Another technique involves immunizing transgenic mice expressing human immunoglobulin genes, such as the XenoMouse®, AlivaMab Mouse or Veloceimmune mouse (see, e.g., Lonberg et al., W093/1222, U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, and WO 91/10741). Another technique is phage display (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332). In these methods, libraries of phage are produced in which members display different antibodies on their outer surfaces. Antibodies are usually displayed as Fv or Fab fragments. Phage displaying antibodies with a desired specificity are selected by affinity enrichment to an α-synuclein peptide or fragment thereof. Another technique is to sequence DNA from human B cells according to the general protocols outlined in Reddy et al., *Nat Biotechnol.* 2010 Sep. 28 (9):965-9 (Epub 2010 Aug. 29), and US 20110053803, 20100099103, 20100291066, 20100035763, and 20100151471. Briefly, B cells can be obtained from a human suspected of having anti-α-synuclein antibodies, e.g., a human immunized with α-synuclein, fragments thereof, longer polypeptides containing α-synuclein or fragments thereof, or anti-idiotypic antibodies. The mRNA of the antibodies from B cells is then reverse transcribed into cDNA and sequenced using, e.g., 454 sequencing technology. After obtaining the sequences of the chains from each antibody, the chains can be paired together (e.g., using bioinformatics), cloned, expressed, and screened for desired properties.

F. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to VH region leader peptide encompassing the translation initiation codon as the 5' primer and a g2b constant regions specific 3' primer. Exemplary primers are described in U.S. patent publication US 2005/0009150 by Schenk et al. (hereinafter, "Schenk"). The sequences from multiple, independently-derived clones, can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner as the VH region. In one approach, a consensus primer set designed for amplification of VL regions is designed to hybridize to the VL region encompassing the translation initiation codon, and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions. Exemplary sequences encoding human constant regions include SEQ ID NO: 37, which encodes a human IgG1 constant region, and SEQ ID NO: 39, which encodes a human kappa light chain constant region.

In one approach, the heavy and light chain variable regions are re-engineered to encode splice donor sequences downstream of the respective VDJ or VJ junctions, and cloned into the mammalian expression vector, such as pCMV-hγ1 for the heavy chain, and pCMV-Mc1 for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hrs. post-transfection and assayed by western blot analysis for antibody production or ELISA for antigen binding. The chimeric antibodies are humanized as described above.

Chimeric, veneered, humanized, and human antibodies are typically produced by recombinant expression. Recombinant nucleic acid constructs typically include an expression control sequence operably linked to the coding sequences of antibody chains, including naturally associated or heterologous expression control element(s), such as a promoter. Once the vector has been incorporated into the appropriate host, the host is maintained under conditions suitable for high level expression of the nucleotide sequences, and the collection and purification of the cross reacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host useful for cloning the DNA sequences encoding the polypeptides disclosed herein. Microbes, such as yeast are also useful for expression. *Saccharomyces* is a yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a host cell for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed, and include CHO cell lines, various COS cell lines, HeLa cells, L cells, human embryonic kidney cell, and myeloma cell lines. The cells can be nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., J. Immunol. 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes, or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carboydrate-oligosaccharide mapping, mass spectrometery, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, Protein Purification (Springer-Verlag, NY, 1982)).

Methodology for commercial production of antibodies can be employed, including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 6,114,148, 6,063,598, 7,569,339, W02004/050884, W02008/012142, W02008/012142, W02005/019442, W02008/107388, and W02009/027471, and U.S. Pat. No. 5,888,809).

G. Antibody Screening Assays

Antibodies can be subject to several screens including binding assays, functional screens, screens in animal models of diseases associated with α-synuclein deposits, and clinical trials. Binding assays test for specific binding and, optionally, affinity and epitope specificity to α-synuclein (or a fragment thereof, such as amino acid residues 118-126). Such screens are sometimes performed in competition with an exemplary antibody such as 5C1. Optionally, either the antibody or α-synuclein target is immobilized in such assay. Functional assays can be performed in cellular models including cells naturally expressing α-synuclein or transfected with DNA encoding α-synuclein or a fragment thereof. Suitable cells include neuronal cells. Cells can be screened for reduced levels of α-synuclein (e.g., by Western blotting or immunoprecipitation of cell extracts or supernatants), reduced levels of aggregated α-synuclein (e.g., by immunohistochemical and/or confocal methods), and/or reduced toxicity attributable to α-synuclein.

Animal model screens test the ability of the antibody to therapeutically or prophylactically treat signs or symptoms in an animal model simulating a human disease associated with α-synuclein deposits, such as a Lewy Body disease. Suitable signs or symptoms that can be monitored include motor balance, coordination, and cognitive deficits. The extent of impairment can be determined by comparison with an appropriate control, such as motor balance, coordination, or cognitive deficiency in control animals that have received a control antibody (e.g., an isotype matched control antibody), a placebo, or no treatment at all. Transgenic or other animal models of Lewy Body diseases can express a human α-synuclein transgene. To facilitate testing in animal models, antibodies having a constant region appropriate for the animal model can be used. It can be concluded that a humanized version of an antibody will be effective if the corresponding mouse antibody or chimeric antibody is effective in an appropriate animal model and the humanized antibody has similar binding affinity (e.g., by a factor of 1.5, 2, or 3, within experimental error).

Clinical trials test for safety and efficacy in a human having a disease associated with α-synuclein deposits.

H. Nucleic Acids

The invention further provides nucleic acids encoding any of the heavy and light chains described above. Typically, the nucleic acids also encode a signal peptide fused to the mature heavy and light chains. Suitable example of signal peptides include amino acid residues 1-19 of SEQ ID NO: 6 (encoded by nucleotides 1-57 of SEQ ID NO: 5) and amino acid residues 1-19 of SEQ ID NO: 8 (encoded by nucleotides 1-57 of SEQ ID NO: 7). Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

V. Therapeutic Applications

The invention provides several methods of treating or effecting prophylaxis of Lewy Body diseases in patients suffering from or at risk of such a disease. Patients amenable to treatment include individuals at risk of disease of a LBD but not showing symptoms, as well as patients presently showing symptoms or the early warning signs of synucleinopathies, for example, EEG slowing, neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia) and miscellaneous other signs and symptoms (fatigue, diplopia, blurred vision, seborrhea, weight loss/gain). Therefore, the present methods can be administered prophylactically to individuals who have a known genetic risk of a LBD. Such individuals include those having relatives who have experienced this disease, and those whose risk is determined by analysis of genetic or biochemical markers. Genetic markers of risk toward PD include mutations in the α-synuclein or Parkin, UCHLI, and CYP2D6 genes; particularly mutations at positions 30 and 53 of the α-synuclein gene. Individuals presently suffering from Parkinson's disease can be recognized from its clinical manifestations including resting tremor, muscular rigidity, bradykinesia and postural instability.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to a therapeutic agent (e.g., a truncated form of α-synuclein peptide) over time. If the response falls, a booster dosage is indicated.

The invention provides methods of treating or effecting prophylaxis of Lewy Body disease in a patient by administration of antibody compositions under conditions that generate a beneficial therapeutic response in the patient (e.g., reduction of neuritic and/or axonal alpha synuclein aggregates, reduction of neuritic dystrophy, improving cognitive function, and/or reversing, treating or inhibiting cognitive decline) in the patient. In some methods, the areas of neuritic dystrophy in the neuropil of neocortex and/or basal ganglia can be reduced by 10%, 20%, 30%, 40% or more as compared to a control.

Cognitive impairment, progressive decline in cognitive function, changes in brain morphology, and changes in cerebrovascular function are commonly observed in patients suffering from or at risk of Lewy Body disease. The invention provides methods of inhibiting decline of cognitive function in such patients.

The invention also provides methods of preserving or increasing synaptic density and/or dentritic density. An index of changes in synaptic or dentritic density can be measured by markers of synapse formation (synaptophysin) and/or dendrites (MAP2). In some methods, the synaptic or dentritic density can be restored to the level of synaptic or dentritic density in a healthy subject. In some methods, the level of synaptic or dentritic density in a patient can be elevated by 5%, 10%, 15%, 20%, 25%, 30% or more as compared to a control.

VI. Pharmaceutical Compositions and Methods Of Treatment

In prophylactic applications, an antibody or a pharmaceutical composition the same is administered to a patient susceptible to, or otherwise at risk of a disease in a regime (dose, frequency and route of administration) effective to reduce the risk, lessen the severity, or delay the onset of at least one sign or symptom of the disease. In some prophylactic applications, the regime is effective to inhibit or delay accumulation of alpha synuclein and truncated fragments in the brain, and/or inhibit or delay its toxic effects and/or inhibit/or delay development of behavioral deficits. In therapeutic applications, an antibody is administered to a patient suspected of, or already suffering from a Lewy body disease in a regime (dose, frequency and route of administration) effective to ameliorate or at least inhibit further deterioration of at least one sign or symptom of the disease. In some therapeutic applications, the regime is effective to reduce or at least inhibit further increase of levels of alpha synuclein and truncated fragments, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses vary depending on many different factors, including means of administration, target site, physiological state of the patient including type of Lewy body disease, whether the patient is an ApoE carrier, whether the patient is human or an animal, other medications administered, and whether treatment is prophylactic or therapeutic.

An exemplary dosage range for antibodies is from about 0.01 to 5 mg/kg, and more usually 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

Antibodies can be administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal or intramuscular. Some routes for administration of antibodies are intravenous and subcutaneous. This type of injection is most typically performed in the arm or leg muscles. In some methods, antibodies are injected directly into a particular tissue where deposits have accumulated, for example intracranial injection.

Pharmaceutical compositions for parenteral administration are can be sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Parkinson's disease, immunotherapy against alpha synuclein WO/2008/103472, Levodopa, dopamine agonists, COMT inhibitors, MAO-B inhibitors, Amantadine, or anticholinergic agents can be used in combination with the present regimes.

VII. Other Applications

The antibodies described above can be used for detecting α-synuclein in the context of clinical diagnosis or treatment or in research. The antibodies can also be sold as research reagents for laboratory research in detecting cells bearing α-synuclein and their response to various stimuli. In such uses, monoclonal antibodies can be labeled with fluorescent molecules, spin-labeled molecules, enzymes or radioisotypes, and can be provided in the form of kit with all the necessary reagents to perform the assay for α-synuclein. The antibodies can also be used to purify α-synuclein, e.g., by affinity chromatography.

The antibodies can be used for detecting LBs in a patient. Such methods are useful to diagnose or confirm diagnosis of PD, or other disease associated with the presence of LBs in the brain, or susceptibility thereto. For example, the methods can be used on a patient presenting with symptoms of dementia. If the patient has LBs, then the patient is likely suffering from a Lewy body disease, such as Parkinson's disease. The methods can also be used on asymptomatic patients. Presence of Lewy bodies or other abnormal deposits of α-synuclein indicates susceptibility to future symptomatic disease. The methods are also useful for monitoring disease progression and/or response to treatment in patients who have been previously diagnosed with a Lewy body disease.

The methods can be performed by administering an antibody and then detecting the antibody after it has bound. If desired, the clearing response can be avoided by using an antibody fragment lacking a full-length constant region, such as a Fab. In some methods, the same antibody can serve as both a treatment and diagnostic reagent.

For diagnosis (e.g., in vivo imaging), the antibodies can be administered by intravenous injection into the body of the patient, or directly into the brain by intracranial injection or by drilling a hole through the skull. The dosage of reagent should be within the same ranges as for treatment methods. Typically, the antibody is labeled, although in some methods, the antibody is unlabeled and a secondary labeling agent is used to bind to the antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size and/or intensity of labeled loci to corresponding base line values. The base line values can represent the mean levels in a population of undiseased individuals. Base line values can also represent previous levels determined in the same patient. For example, base line values can be determined in a patient before beginning treatment, and measured values thereafter compared with the base line values. A decrease in values relative to base line signals a positive response to treatment.

The antibodies can be used to generate anti-idiotype antibodies. (see, e.g., Greenspan & Bona, FASEB J. 7 (5):437-444, 1989; and Nissinoff, J. Immunol. 147:2429-2438, 1991). Such anti-idiotype antibodies can be utilized in pharmacokinetics, pharmacodynamics, biodistribution studies as well as in studies of clinical human-anti-human antibody (HAHA) responses in individuals treated with the antibodies. For example, anti-idiotypic antibodies bind specifically the variable region of humanized 5C1 antibodies and therefore can be used to detect humanized 5C1 antibodies in pharmacokinetic studies and help to quantify human-anti-human antibody (HAHA) responses in treated individuals.

VIII. Kits

Also provided are kits including an α-synuclein-specific antibody and instructions for use. Such kits can be used for, e.g., performing the diagnostic methods described above. A kit can also include a label. Kits also typically contain labeling providing directions for use of the kit. The labeling may also include a chart or other correspondence regime correlating levels of measured label with levels of antibodies to α-synuclein. The term labeling generally refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Also provided are diagnostic kits for performing in vivo imaging. Such kits typically contain an antibody binding to an epitope of α-synuclein as described herein. The antibody can be labeled or a secondary labeling reagent is included in the kit. The kit can include instructions for performing an in vivo imaging assay.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1

Isolation of Murine 5C1

The murine 5C1 antibody was generated in a mouse injected with a peptide conjugate containing the peptide immunogen VDPDNEAYEGGC (SEQ ID NO: 14) coupled to a sheep anti- mouse antibody. The peptide, which includes residues 118-126 of α-synuclein fused to a C-terminal GGC peptide, was coupled to the sheep anti-mouse antibody via a maleimide linker bound to the C-terminal cysteine residue.

Example 2

Passive Immunization with α-Synuclein Antibodies

To test the effect of α-synuclein antibodies on an animal model for Lewy Body disease, various α-synuclein antibodies were used to passively immunize mice. 3-4 month old wildtype, α-synuclein knockout, and α-synuclein transgenic (line 61) female mice were used (n=14/group). Antibodies that were tested included:

9E4 (IgG1, epitope: amino acids 118-126 of α-synuclein);

5C1 (IgG1, immunogen: amino acids 118-126 of α-synuclein, cys-linker);

5D12(IgG2, immunogen: amino acids 118-126 of α-synuclein, n-linker);

1H7 (IgG1, epitope: amino acids 91-99 of α-synuclein); and 27-1 (IgG1 control antibody).

Mice received an antibody dosage of 10 mg/kg over a 5 month period, for a total of 21 injections. In addition, the animals were injected with lentivirus (LV) expressing human α-synuclein (wt) by unilateral introduction of human α-synuclein (wt) into the hippocampus.

Readout antibodies included α-synuclein antibodies from Chemicon (epitope: full-length α-synuclein), Millipore (epitope: full-length α-synuclein), and ELADW 105 (epitope: amino acids 121-124 of α-synuclein, preferably with α-synuclein truncated at residue 122-124).

Endpoints: Antibody titers were monitored prior to termination of the experiment. Behavior was assessed using the Morris Water Maze (MWM) and horizontal round beam tests. The round beam test assesses motor balance, coordination, and gait using two beams of varying diameter. Beam A (the training beam) is larger in diameter, and therefore easier to traverse. Beam D (the testing beam) is smaller in diameter, and therefore more difficult to traverse. Water maze performance was carried out at weeks 10 and just prior to termination. On termination of the experiment, mice were sacrificed and neuropathology measurements were obtained for α-synuclein aggregation, synaptophysin, and MAP2. In addition, biochemistry measurements were obtained for α-synuclein, PSD95, and synaptophysin. Selected multilabeling and confocal labeling were carried out using synaptic, neuronal and glial markers.

Results: The results showed that all antibodies, except 5D12, produced significant reduction in α-syn accumulation and preservation of synaptic and dendritic densities, as well as positive outcomes in MWM performance. The 9E4 antibody was effective in in vitro and in vivo studies as well as behavioral assays. In particular, the results indicate that α-synuclein antibodies may reduce neuritic/axonal α-synuclein aggregates.

Figure 4:
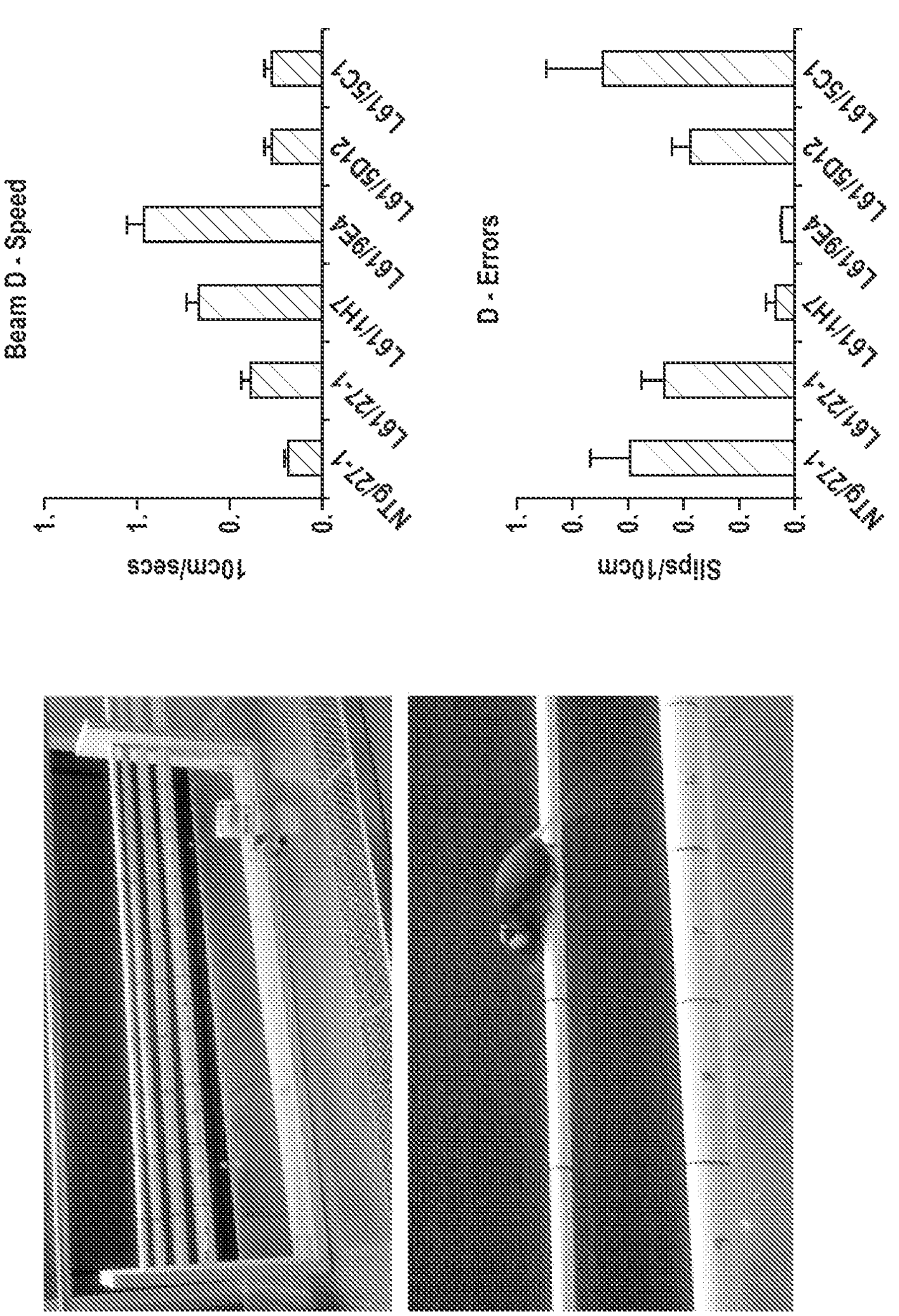
FIG. 4 shows the results of passive immunotherapy with 5C1 on speed and errors in the round beam test.

Behavioral Results: The 5C1 and 9E4 antibodies improved water maze performance in α-synuclein transgenic mice, as did 1H7, albeit to a lesser extent. See FIG. 3. In contrast, the 5D12 antibody did not improve water maze performance in α-synuclein transgenic mice. With regard to the horizontal round beam test, the 9E4 and 1H7 antibodies improved performance as measured both by speed and number of errors, whereas the 5D12 and 5C1 antibodies did not. See FIG. 4. The data in FIG. 4 is presented as the number of slips/10 cm (i.e., "errors") and the ratio of distance traveled divided by time taken to travel the distance (i.e., "speed," measured in units of 10 cm/sec).

Neuropathology Results: The 5C1, 9E4, and 1H7 antibodies reduced ELADW-105 positive neuritic dystrophy, whereas the 5D12 antibody did not. In α-synuclein transgenic mice, the 9E4 antibody reduced the area of neuropil by 43% in the neocortex and by 40% in the basal ganglia, as compared to control mice (i.e., mice receiving the 27-1 IgG1 control antibody). The 9E4 antibody also preserved staining for synaptophysin and MAP2 in the neocortex and basal ganglia.

Example 3

Sequencing of Variable Domains of 5C1 mRNA was extracted and purified from a 5C1 hybridoma cell pellet using QIAGEN® OLIGOTEX® mRNA kit. Purified mRNA was next transcribed into cDNA using an oligo dT anti-sense primer and the INVITROGEN® SUPERSCRIPT® II kit. Nucleic acid sequences coding for the 5C1 heavy chain and light chain variable regions were amplified from the cDNA by PCR, using degenerate VH and VL sense primers and a gene-specific (CH/CL) anti-sense primer. The PCR products, which were designed to include the sequence of the signal peptide, variable domain, and constant domain (up to the anti-sense primer), were gel-purified, cloned into a blunt vector or TA vector, and then sequenced. Sequences were deduced from analysis of at least 3 independent clones having an open reading frame starting with a methionine and extending through the variable region into the constant region.

Nucleic acid encoding the 5C1 heavy chain variable region has the sequence of SEQ ID NO: 5. The corresponding protein sequence (FIG. 1), which includes a signal peptide at positions 1-19 (underlined) is as follows:

```
                                       (SEQ ID NO: 6)
MERHWIFLFLLSVTGGVHSQVQLQQSGAELAKPGTSVQMSCKASGYTFT

NYWMNWIKARPGQGLEWIGATNPNNGYTDYNQRFKDKAILTADKSSNTA

YMHLSSLTSEDSAVYFCASGGHLAYWGQGTVVTVSA
```

Nucleic acid encoding the 5C1 light chain variable region has the sequence of SEQ ID NO: 7. The corresponding protein sequence (FIG. 2), which includes a signal peptide at positions 1-19 (underlined) is as follows:

```
                                       (SEQ ID NO: 8)
MKLPVRLLVLMFWIPASSSDVVMTQIPLYLSVSPGDQASISCRSSQSLF

HSKGNTYLHWYLQKPGQSPKLLINRVSNRFSGVPDRFSGSGSGTDFTLK

ISGVEAEDLGVYFCSQSAHVPWTFGGGTKLEIR
```

The amino acid sequence for the mature 5C1 heavy chain variable region (SEQ ID NO: 9) is shown in FIGS. 10A-D, and the corresponding amino acid sequence for the mature 5C1 light chain variable region (SEQ ID NO: 24) is shown in FIGS. 11A-D. Kabat numbering is used throughout.

Example 4

Humanization of Murine 5C1

Analysis of the CDRs of the 3H6 Vh region reveals a 5 residue CDR-H1 (SEQ ID NO: 10), a 17 residue CDR-H2 (SEQ ID NO: 11), and a 6 residue CDR-H3 (SEQ ID NO: 12). Similar analysis of the CDRs of the 3H6 Vk region reveals a 16 residue CDR-L1 (SEQ ID NO: 25), a 7 residue CDR-L2 (SEQ ID NO: 26), and a 9 residue CDR-L3 (SEQ ID NO: 27).

Analysis of the residues at the interface between the 5C1 Vk and Vh regions reveals that most of the residues are the ones commonly found.

A search of the non-redundant protein sequence database from NCBI allowed selection of suitable human frameworks into which to graft the 5C1 murine CDRs. For Vk, a human kappa light chain with NCBI accession code CAB51293.1 (GI:5578786; SEQ ID NO: 28) was chosen. For Vh, human Ig heavy chain AAY42876.1 (GI:66096557; SEQ ID NO: 13) was chosen.

Exemplary humanized Vh and Vk designs, with backmutations based on the selected human frameworks, are shown in FIGS. 10A-D and FIGS. 11A-D, respectively.

Exemplary Humanized Vh Designs

Five different humanized versions of the 5C1 Vh region were designed, H1, H2, H3, H4, and H5. In selecting backmutations, residues H11, H27, H30, H48, H67, H69, H73, H91, and H94 were ultimately focused on. In each of the humanized Vh region designs, residues H11, H27, H30, H48, and H73 were backmutated to L, Y, T, I, and K, respectively, because the residues formed part of CDR-H1 according to the Chothia definition (H27 and H30) or the corresponding residues in the human framework sequence are low frequency residues (V at position H11, M at position H48, and E at position H73). For version H1 (SEQ ID NO: 14), additional residues H67 and H69 were backmutated (to A and L, respectively) to preserve CDR packing. In version H2 (SEQ ID NO: 15), no further backmutations were introduced (i.e., the backmutations at positions H67 and H69 in version H1 were eliminated). In version H3 (SEQ ID NO: 16), additional residues H67, H69, H91, and H94 were backmutated (to A, L, F, and S, respectively). The H67, H69, and H94 backmutations were to preserve CDR packing, while H91, a Vh/Vk interface residue, was backmutated to test its impact on the interface. In version H4 (SEQ ID NO: 17), additional residues H67, H69, and H94 were backmutated (to A, L, and S, respectively). Thus, version H4 differs from H3 in that the backmutation at H91 is eliminated. In version H5 (SEQ ID NO: 18), additional residue H94 was also backmutated (to S), to preserve CDR packing.

Exemplary nucleic acid sequences encoding humanized 5C1 H1, H2, H3, H4, and H5 are provided in SEQ ID NOs: 19, 20, 21, 22, and 23, respectively.

Exemplary Humanized Vk Designs

Four different humanized versions of the 5C1 Vk region were designed, L1, L2, L3, and L4. In selecting backmutations, residues L2, L12, L14, L45, L49, and L87 were ultimately focused on. In each of the humanized Vk region designs, residues L12 and L14 were backmutated to S because the corresponding residues in the human framework sequence (P and T, respectively) are low frequency residues. For version L1 (SEQ ID NO: 29), additional residues L2, L45, L49, and L87 were backmutated (to V, K, N, and F, respectively). L2 is a canonical/CDR interacting residue; L45 undergoes a polarity/charge switch from the murine to human framework sequences (K to Q), and thus could impact folding; L49 is a Vernier residue; and L87 is a Vh/Vk interface residue. In version L2 (SEQ ID NO: 30), additional residue L45 was backmutated to K. Thus, relative to L1, the backmutations at residues L2, L49, and L87 were eliminated. In version L3 (SEQ ID NO: 31), additional residues L2, L49, and L87 were backmutated (to V, N, and F, respectively). Thus, relative to L1, the backmutation at residue L45 was eliminated. In version L4 (SEQ ID NO: 32), no additional residues were backmutated (i.e., only residues L12 and L14 were backmutated).

Exemplary nucleic acid sequences encoding humanized 5C1 L1, L2, L3, and L4 are provided in SEQ ID NOs: 33, 34, 35, and 36, respectively.

Example 5

Affinity of Humanized 5C1 Antibodies for Alpha-Synuclein

Figure 5:
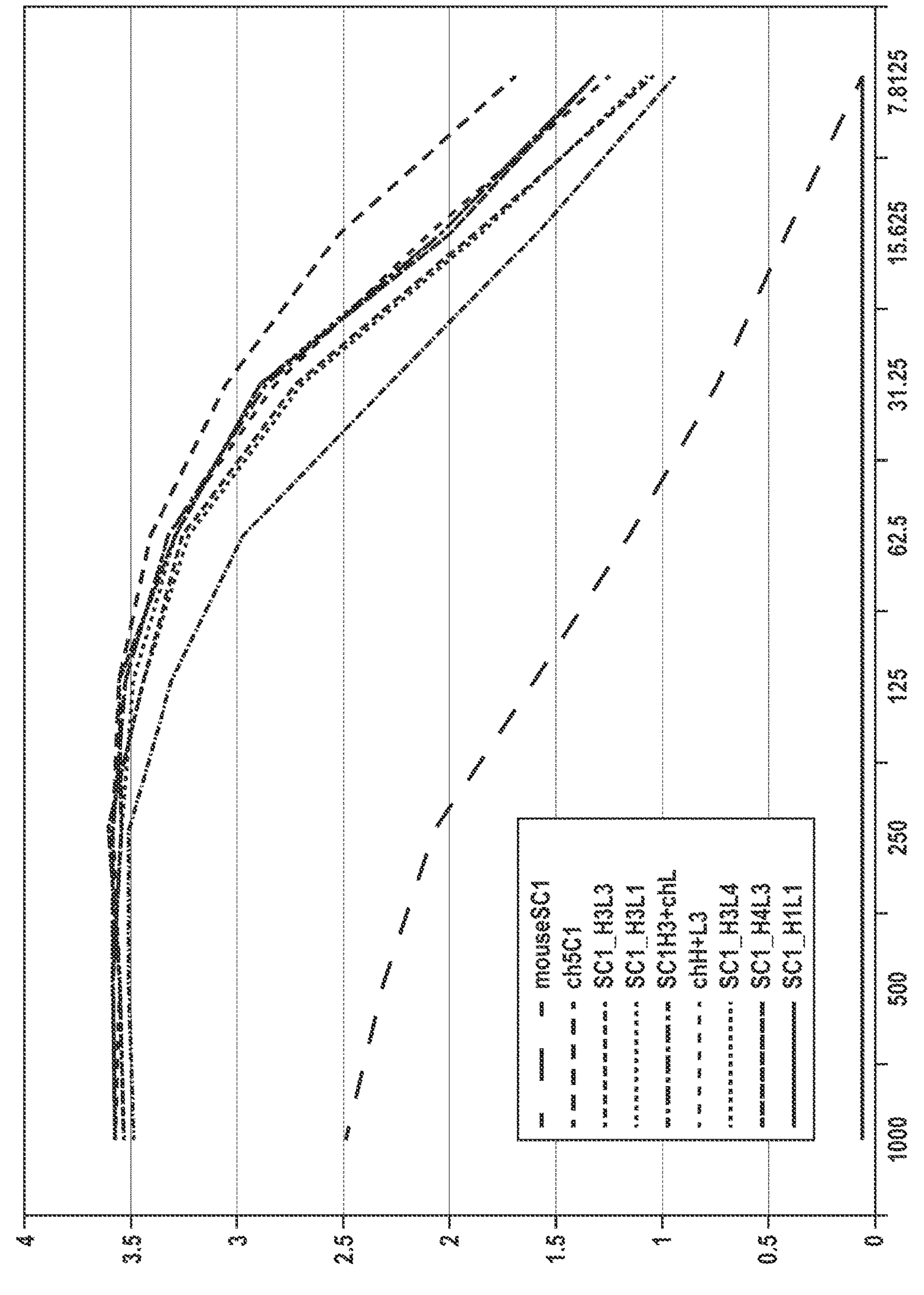
FIG. 5 shows the results of an ELISA assay testing the affinity of different humanized 5C1 antibodies.

The affinity of various combinations of 5C1 humanized heavy chains and humanized light chain proteins for α-synuclein was analyzed by ELISA. As shown in FIG. 5, the H1L1 version of humanized 5C1 antibody displayed no affinity for α-synuclein under the assay conditions. In contrast, the chimeric 5C1 antibody had a higher affinity for α-synuclein than the murine 5C1 antibody. Humanized versions H3L4, H4L3, and chimeric H+L3 performed comparably, and almost as well as the chimeric 5C1 antibody. In addition, humanized versions H3L3 and H3L1 performed comparably, though with slightly lower affinity than H3L4, H4L3, and chimeric H+L3.

Various humanized 5C1 antibody versions were also analyzed by Biacore, to more precisely determine binding affinities. An anti-human IgG CMS Biacore chip was prepared following the protocol supplied by GE Healthcare. Each humanized 5C1 antibody version was independently captured to a level were $R_{max}$ would not exceed 50, using the equation:

$$R_{max}=\text{(RU of captured antibody)*(MW of Synuclein)/(MW of captured antibody)*2}$$

The factor of 2 in the denominator is for the number of binding sites on the antibody. Alpha synuclein was flowed over the chop at a concentration varied from ~10× above the expected KD to ~10× below the expected KD. Data was collected and double reference subtracted to account for drift and a small amount of nonspecific binding. The data was analyzed using BIAcore evaluation software using a 1:1 model and a global fit.

The results of the Biacore analysis are summarized in Table 1 (below). The data indicates that most of the loss in affinity for alpha synuclein is due to an increased off rate in some of the antibody versions. Based on the affinity data, H4L3 was identified as a preferred antibody.

Table 1: Biacore-Determined Affinities of 5C1 Variant Antibodies

TABLE 1

Biacore-Determined Affinities of 5C1 Variant Antibodies

| 5C1 Variant | # Framework Mouse AAs HC | # Framework Mouse AAs LC | $K_D$ | $K_{on}$ | $K_{off}$ |
|---|---|---|---|---|---|
| m5C1 | 82 | 80 | 68.7 nM | 7.5 × $10^4$/s | 5.1 × $10^3$/s |
| Ch5C1 | 82 | 80 | 86.0 nM | 6.1 × $10^4$/s | 5.3 × $10^3$/s |
| h5C1_H3L4 | 65, incl. 9 backmutations (V11L, G27Y, N30T, M48I, V67A, I69L, E73K, Y91F, R94S) | 69, incl. 2 backmutations (P12S, T14S) | 1237.0 nM | 4.4 × $10^4$/s | 54.5 × $10^3$/s |
| h5C1_H4L3 | 64, incl. 8 backmutations (V11L, G27Y, N30T, M48I, V67A, I69L, E73K, R94S) | 72, incl. 5 backmutations (I2V, P12S, T14S, Y49N, Y87F) | 119.8 nM | 4.4 × $10^4$/s | 5.1 × $10^3$/s |
| h5C1_H4L4 | | 69, incl. 2 backmutations (P12S, T14S) | 600.9 nM | 5.3 × $10^4$/s | 32.4 × $10^3$/s |
| h5C1_H5L3 | 62, incl. 6 backmutations (V11L, G27Y, N30T, M48I, E73K, R94S) | 72, incl. 5 backmutations (I2V, P12S, T14S, Y49N, Y87F) | 283.1 nM | 3.9 × $10^4$/s | 11.1 × $10^3$/s |
| h5C1_H5L4 | | 69, incl. 2 backmutations (P12S, T14S) | 1062.0 nM | 3.7 × $10^4$/s | 40.3 × $10^3$/s |

Example 6

Alanine Scanning Mutagenesis

The epitopes bound by antibodies 5C1, 9E4 and 5D12 have been approximately mapped to being within residues 118-126 of alpha synuclein due to the antibodies binding to overlapping peptides. This example describes a more precise mapping, by alanine scanning mutagenesis, of each residue between positions 118 and 126 of alpha synuclein. Alanine is used because of its non-bulky, chemically inert, methyl functional group that nevertheless mimics the secondary structure preferences that many of the other amino acids possess. The upper portions of FIGS. 6, 7 and 8 show the results of Western blots stained with antibodies 9E4, 5C1 and 5D12, respectively. The blots include full-length alpha synuclein and point mutants of alpha synuclein produced by alanine scanning mutagenesis of residues 118-126 and were stained with 0.5 μg/ml of antibody. Mutations at positions 122 and 125 essentially abolish binding of 9E4, whereas mutations at other positions have little if any effect. Thus, 9E4 predominantly contacts residues 122 and 125. Mutations at positions 120-122 essentially abolish binding of 5C1, and mutations at positions 123 and 124 substantially reduce but do not abolish binding. Thus, 5C1 predominantly contacts residues 120-122 and, to a lesser extent, residues 123-124. Mutations at positions 120-122 essentially abolished binding of 5D12, and mutations at positions 118, 119, 123 and 124 substantially reduced but did not abolish binding. Thus, 5D12 binds predominantly to positions 120-122 and, to a lesser extent, positions 118, 119, 123, and 124. In each of FIGS. 6-8, 1H7 antibody is used as a control. 1H7 binds to residues 91-98 of alpha synuclein, and therefore is expected to bind to the alpha synuclein regardless of presence of mutations in residues 118-126.

The different binding specificities of 9E4 compared to 5C1 and 5D12 may in part reflect their respective methods of production. 9E4 was made by immunization with full-length alpha synuclein resulting in an antibody binding a conformational epitope. 5C1 and 5D12 were made by immunizing with a peptide of 10 amino acids resulting in a linear epitope.

Figure 9:
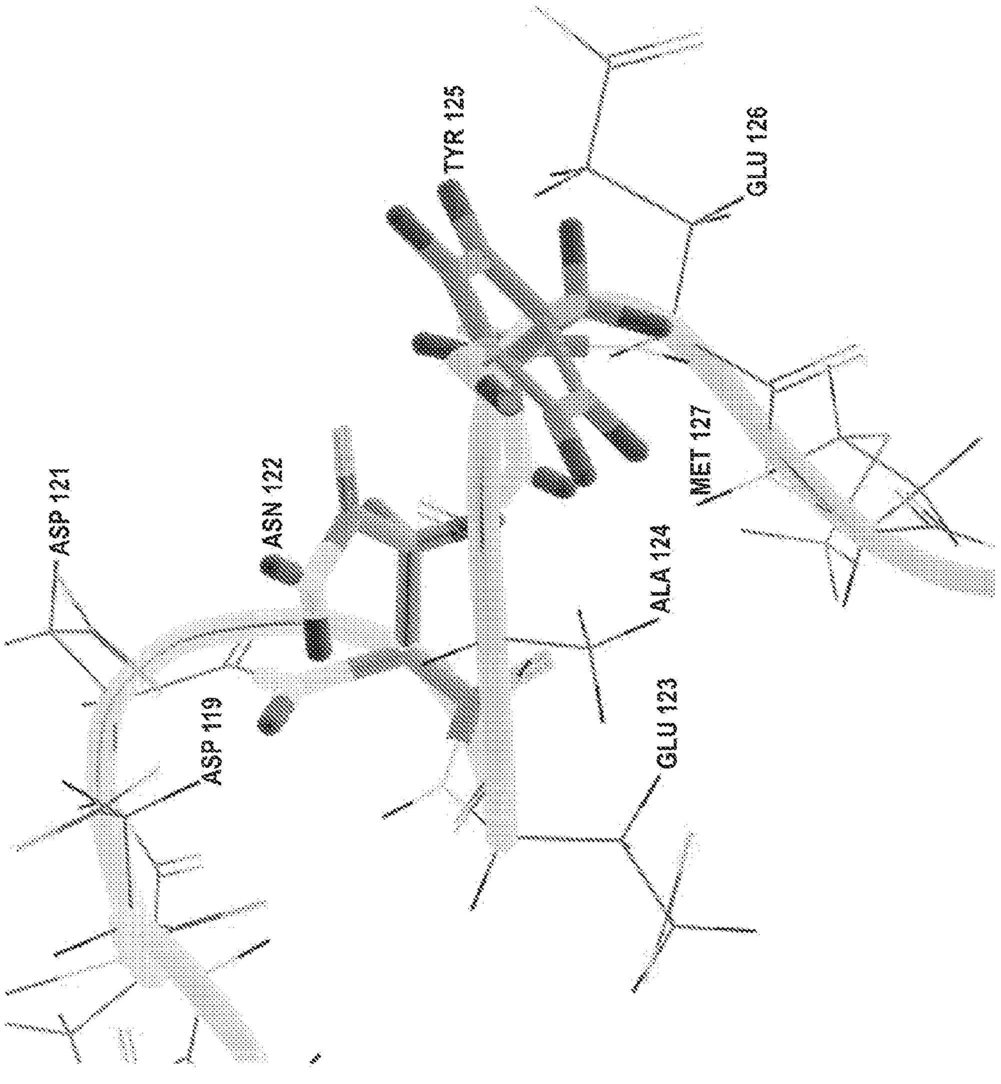
FIG. 9 depicts a ball and stick model of the amino acids of α-synuclein proximate to the binding sites of the 9E4, 5C1 and 5D12 antibodies.

FIG. 9 is a ball and stick model of the amino acids in alpha synuclein proximate to the binding sites of the 9E4, 5C1 and 5D12 antibodies. The two discontinuous residues of the epitope bound by 9E4, residues 122 and 125, form a pocket in the conformation of the full-length alpha synuclein protein.

Many changes and modifications can be made thereto without departing from the spirit or scope of the appended claims. Unless otherwise apparent from the context, any step, feature, embodiment, or aspect can be used in combination with any other. All publications, patent filings, web sites, accession numbers and the like mentioned in this specification are herein incorporated by reference in their entirety to the same extent as if each individual publication or patent application was specifically and individually indicated to be incorporated by reference. To the extent different versions of a citation exist, the most recent version at the effective filing date of the application is meant.

What is claimed is:

1. A method of treating, reducing risk, lessening severity or delaying onset of a Lewy body disease in a patient having or at risk of a Lewy body disease comprising administering to the patient an effective regime of an antibody comprising three light chain CDRs and three heavy chain CDRs of monoclonal antibody 5C1, wherein 5C1 is a mouse antibody characterized by a heavy chain variable region having an amino acid sequence comprising SEQ ID NO: 9 and light chain variable region having an amino acid sequence comprising SEQ ID NO: 24 and thereby treating, reducing risk, lessening severity or delaying onset of the disease.

2. The method of claim 1, wherein the disease is Parkinson's disease.

3. The method of claim 1, wherein the disease is multiple system atrophy (MSA) or Dementia with Lewy Bodies (DLB).

4. The method of claim 1, wherein the method inhibits decline of cognitive function in the patient.

5. The method of claim 1, wherein the method reduces neuritic and/or axonal alpha synuclein aggregates.

6. The method of claim 1, wherein the method reduces neuritic dystrophy in the patient.

7. The method of claim 1, wherein the method preserves synaptic and/or dendritic densities.

8. The method of claim 1, where in the antibody comprises three heavy chain CDRs of SEQ ID NO: 9 as defined by Kabat and three light chain CDRs of SEQ ID NO: 24 as defined by Kabat.

9. The method of claim 1, wherein the antibody has a human IgG1 Isotype.

10. The method of claim 1, wherein the antibody comprises a mature heavy chain variable region having an amino acid sequence at least 90% identical to SEQ ID NO: 17 and a mature light chain variable region having an amino acid sequence at least 90% identical to SEQ ID NO: 31, wherein the antibody specifically binds to human alpha synuclein.

11. The method of claim 1, wherein the mature heavy chain variable region is fused to a heavy chain constant region and the mature light chain variable region is fused to a light chain constant region.

12. The method of claim 11, wherein the mature heavy chain variable region is fused to a heavy chain constant region having the sequence of SEQ ID NO: 38 and/or the mature light chain variable region is fused to a light chain constant region having the sequence of SEQ ID NO: 40.

13. The method of claim 11, wherein the mature heavy chain variable region has an amino acid sequence comprising SEQ ID NO: 17 and the mature light chain variable region has an amino acid sequence comprising SEQ ID NO: 31.

14. A method of inhibiting synuclein aggregation or reducing Lewy bodies or synuclein aggregates in a patient having or at risk of a Lewy body disease, comprising administering to the patient an effective amount of an antibody comprising three light chain CDRs and three heavy chain CDRs of monoclonal antibody 5C1, wherein 5C1 is a mouse antibody characterized by a heavy chain variable region having an amino acid sequence comprising SEQ ID NO: 9 and light chain variable region having an amino acid sequence comprising SEQ ID NO: 24 and thereby inhibiting synuclein aggregation or reducing Lewy bodies or synuclein aggregates.

15. The method of claim 14, wherein the disease is Parkinson's disease.

16. The method of claim 14, wherein the disease is multiple system atrophy (MSA) or Dementia with Lewy Bodies (DLB).

17. The method of claim 14, wherein the method inhibits decline of cognitive function in the patient.

18. The method of claim 14, wherein the method reduces neuritic and/or axonal alpha synuclein aggregates.

19. The method of claim 14, wherein the method reduces neuritic dystrophy in the patient.

20. The method of claim 14, wherein the method preserves synaptic and/or dendritic densities.

21. The method of claim 14, wherein the antibody comprises three heavy chain CDRs of SEQ ID NO: 9 as defined by Kabat and three light chain CDRs of SEQ ID NO: 24 as defined by Kabat.

22. The method of claim 14, wherein the antibody has a human IgG1 isotype.

23. The method of claim 14, wherein the antibody comprises a mature heavy chain variable region having an amino acid sequence at least 90% identical to SEQ ID NO: 17 and a mature light chain variable region having an amino acid sequence at least 90% identical to SEQ ID NO: 31, wherein the antibody specifically binds to human alpha synuclein.

24. The method of claim 14, wherein the mature heavy chain variable region is fused to a heavy chain constant region and the mature light chain variable region is fused to a light chain constant region.

25. The method of claim 24, wherein the mature heavy chain variable region is fused to a heavy chain constant region having the sequence of SEQ ID NO: 38 and/or the mature light chain variable region is fused to a light chain constant region having the sequence of SEQ ID NO: 40.

26. The method of claim 24, wherein the mature heavy chain variable region has an amino acid sequence comprising SEQ ID NO: 17 and the mature light chain variable region has an amino acid sequence comprising SEQ ID NO: 31.

* * * * *